(12) United States Patent
Kepler et al.

(10) Patent No.: US 7,677,246 B2
(45) Date of Patent: Mar. 16, 2010

(54) MODULAR PRESSURE SUPPORT SYSTEM

(75) Inventors: Jeffrey Kepler, Export, PA (US); Michael E. Mort, Somerset, PA (US); Richard A. Seman, Jr., Delmont, PA (US); Mark DiMatteo, Irwin, PA (US); Christopher J. McCracken, Monroeville, PA (US); James S. Vreeland, Greensburg, PA (US); Steven B. Radney, Pittsburgh, PA (US); Michael Bobeck, Sarver, PA (US); Allan Cameron, Natick, MA (US); David P. Chastain, Boston, MA (US); Patrick F. McDermott, Oxford, MA (US); William J. Palm, Newtonville, MA (US); Roy A. Thompson, Dorchester, MA (US)

(73) Assignee: RIC Investments, LLC, Wilmington, DE (US)

( * ) Notice: Subject to any disclaimer, the term of this patent is extended or adjusted under 35 U.S.C. 154(b) by 1209 days.

(21) Appl. No.: 11/234,351

(22) Filed: Sep. 23, 2005

(65) Prior Publication Data

US 2007/0169776 A1     Jul. 26, 2007

(51) Int. Cl.
*A61M 11/00* (2006.01)
(52) U.S. Cl. .................. 128/204.18; 128/202.27; 128/204.14
(58) Field of Classification Search ............ 128/204.18, 128/202.27, 204.14, 203.12, 203.18, 203.16, 128/203.14, 204.13, 204.15
See application file for complete search history.

(56) References Cited

U.S. PATENT DOCUMENTS

| 5,588,425 | A   | 12/1996 | Smith |
| 5,673,687 | A   | 10/1997 | Dobson et al. |
| 5,964,923 | A   | 10/1999 | Lokhandwala |
| 6,017,350 | A   | 1/2000  | Long |
| 6,202,642 | B1  | 3/2001  | McKinnon et al. |
| 6,397,841 | B1* | 6/2002  | Kenyon et al. ......... 128/202.27 |
| 6,398,197 | B1  | 6/2002  | Dickinson et al. |
| 6,435,180 | B1  | 8/2002  | Hewson et al. |
| 6,615,830 | B1  | 9/2003  | Serowski et al. |
| 6,635,021 | B1  | 10/2003 | Sullivan et al. |

(Continued)

FOREIGN PATENT DOCUMENTS

| WO | WO 01/32069 A2    | 5/2001 |
| WO | WO 02/066106 A1   | 8/2002 |
| WO | WO 02/066107 A1   | 8/2002 |
| WO | WO 2004/112873 A1 | 12/2004 |

OTHER PUBLICATIONS

U.S. Appl. No. 60/697,140, filed Jul. 7, 2005, Ranwez et al.
U.S. Appl. No. 60/697,141, filed Jul. 7, 2005, Rothermel et al.

*Primary Examiner*—Steven O Douglas
(74) *Attorney, Agent, or Firm*—Michael W. Haas

(57) ABSTRACT

A pressure support system that comprises a patient circuit, a docking assembly, and a tank. The patient circuit delivers a pressurized flow of breathable gas to a patient. The docking assembly has an inlet and an outlet that is adapted to receive the pressurized flow of breathable gas, and is also adapted to be connected with the patient circuit. The tank is constructed and arranged to be removably connected with the docking assembly, and enables the pressurized flow of breathable gas to pass therethrough. The tank is also adapted to contain a liquid such that a humidity level of the pressurized flow of breathable gas is elevated as the pressurized flow of breathable gas passes therethrough.

16 Claims, 23 Drawing Sheets

U.S. PATENT DOCUMENTS

| | | |
|---|---|---|
| 6,694,974 B1 * | 2/2004 | George-Gradon et al. ............ 128/203.17 |
| 6,718,974 B1 | 4/2004 | Moberg |
| 6,851,425 B2 | 2/2005 | Jaffre et al. |
| 6,918,389 B2 | 7/2005 | Seakins et al. |
| 6,929,006 B2 | 8/2005 | Kruger et al. |
| 7,096,864 B1 * | 8/2006 | Mayer et al. ............ 128/202.27 |
| 2003/0005928 A1 | 1/2003 | Appel et al. |
| 2004/0079370 A1 | 4/2004 | Kruger et al. |
| 2004/0226560 A1 | 11/2004 | Lipscombe et al. |
| 2005/0178383 A1 | 8/2005 | Mackie et al. |
| 2005/0247314 A1 | 11/2005 | Virr et al. |

\* cited by examiner

MODULAR PRESSURE SUPPORT SYSTEM

BACKGROUND OF THE INVENTION

1. Field of the Invention

The invention pertains to a gas flow delivery system that provides a pressurized flow of breathable gas to a patient, and, in particular, to as gas flow delivery system with an optional modular humidification system, and universal interface port.

2. Description of the Related Art

Ventilators, pressure support systems, and other respiratory devices that provide a pressurized flow of breathable gas to a patient are known. In some instances, a humidifier may be added to a respiratory device to elevate a humidity level of the gas delivered to the patient. However, conventional interfaces between a humidifier and a respiratory device are often inconvenient to use. In addition, it is often complicated and/or inconvenient to couple and/or uncouple the humidifier to the respiratory device.

Additionally, coupling the humidifier to the respiratory device may inhibit one or more functionalities of the respiratory device. For example, in some instances, the pressure of the gas being delivered to the patient may not be measured accurately when a humidifier is installed. Further, conventional systems may not provide suitable safeguards against fluid that is stored within the humidifier from being spilled into the respiratory device.

Generally, some respiratory devices include a mechanism for retrieving information in an electronic format from the respiratory device regarding the treatment received by the patient from the device. For example, information related to an amount of treatment delivered to a patient, information related to one or more operating conditions, information related to one or more operating parameters, or other information may be retrieved from the respiratory device. However, typically a respiratory device provides for a single mechanism for obtaining this information, such as a modem or a smart card. Therefore, a need exists for a respiratory device that provides a plurality of options for obtaining treatment information electronically.

BRIEF SUMMARY OF THE INVENTION

One aspect of the invention relates to a pressure support system that comprises a patient circuit, a docking assembly, and a tank. The patient circuit delivers a pressurized flow of breathable gas to a patient. The docking assembly has an inlet and an outlet that is adapted to receive the pressurized flow of breathable gas, and is also adapted to be connected with the patient circuit. The tank is constructed and arranged to be removably connected with the docking assembly. The tank is also adapted to contain a liquid such that a humidity level of the pressurized flow of breathable gas is elevated as the pressurized flow of breathable gas passes therethrough.

Another aspect of the invention relates to a method of delivering a pressurized flow of breathable gas to a patient. The method comprises providing the pressurized flow of breathable gas to a docking assembly at an inlet, connecting a patient circuit to an outlet associated with the docking assembly, removably connecting a tank to the docking assembly, the tank being adapted to contain a liquid such that a humidity level of the pressurized flow of breathable gas is elevated as the pressurized flow of breathable gas passes through the tank, wherein removably connecting the tank to the docking assembly places the inlet in communication with the outlet, and delivers the pressurized flow of breathable gas from the inlet to the outlet while elevating the humidity level of the pressurized flow of breathable gas, and delivering the pressurized flow of breathable gas from the outlet to the patient along the patient circuit.

Another aspect of the invention relates to a gas flow generating system that generates a pressurized flow of breathable gas for delivery to a patient. The system comprises a control unit and an accessory interface. The control unit controls one or more aspects of operation of the gas flow generating system. The accessory interface removably connects with a modular accessory to place the modular accessory in communication with the control unit such that information can be transferred from the modular accessory to the control unit and from the control unit to the modular accessory via the accessory interface.

Another aspect of the invention relates to a modular accessory that selectively interfaces with a gas flow generating system that generates a pressurized flow of breathable gas for delivery to a patient. The modular accessory comprises a delivery system interface and a communication unit. The delivery system interface removably connects with the gas flow generating system to place the modular accessory in communication with the gas flow generating system such that information can be transferred from the modular accessory to the gas flow generating system and from the gas flow generating system to the modular accessory via the accessory interface. The communication unit outputs the information transferred from the gas flow generating system to the modular accessory.

Another aspect of the invention relates to a pressure support system that comprises a gas flow generating system, a tank, a patient circuit, a conduit, and a barrier. The gas flow generating system generates a pressurized flow of breathable gas. The tank enables the pressurized flow of breathable gas to pass therethrough, and is adapted to contain a liquid such that a humidity level of the pressurized flow of breathable gas is elevated as the pressurized flow of breathable gas passes therethrough. The patient circuit delivers the pressurized flow of breathable gas to a patient. The conduit is connected at one end to an outlet of the gas flow generating system and at the other end to an inlet of the tank so as to communicate the pressurized flow of breathable gas from the gas flow generating system to the tank. The barrier is formed within the conduit, and inhibits the liquid contained by the tank from ingressing on the gas flow generating system when the liquid is introduced into the conduit.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENT(S)

Figure 1A:
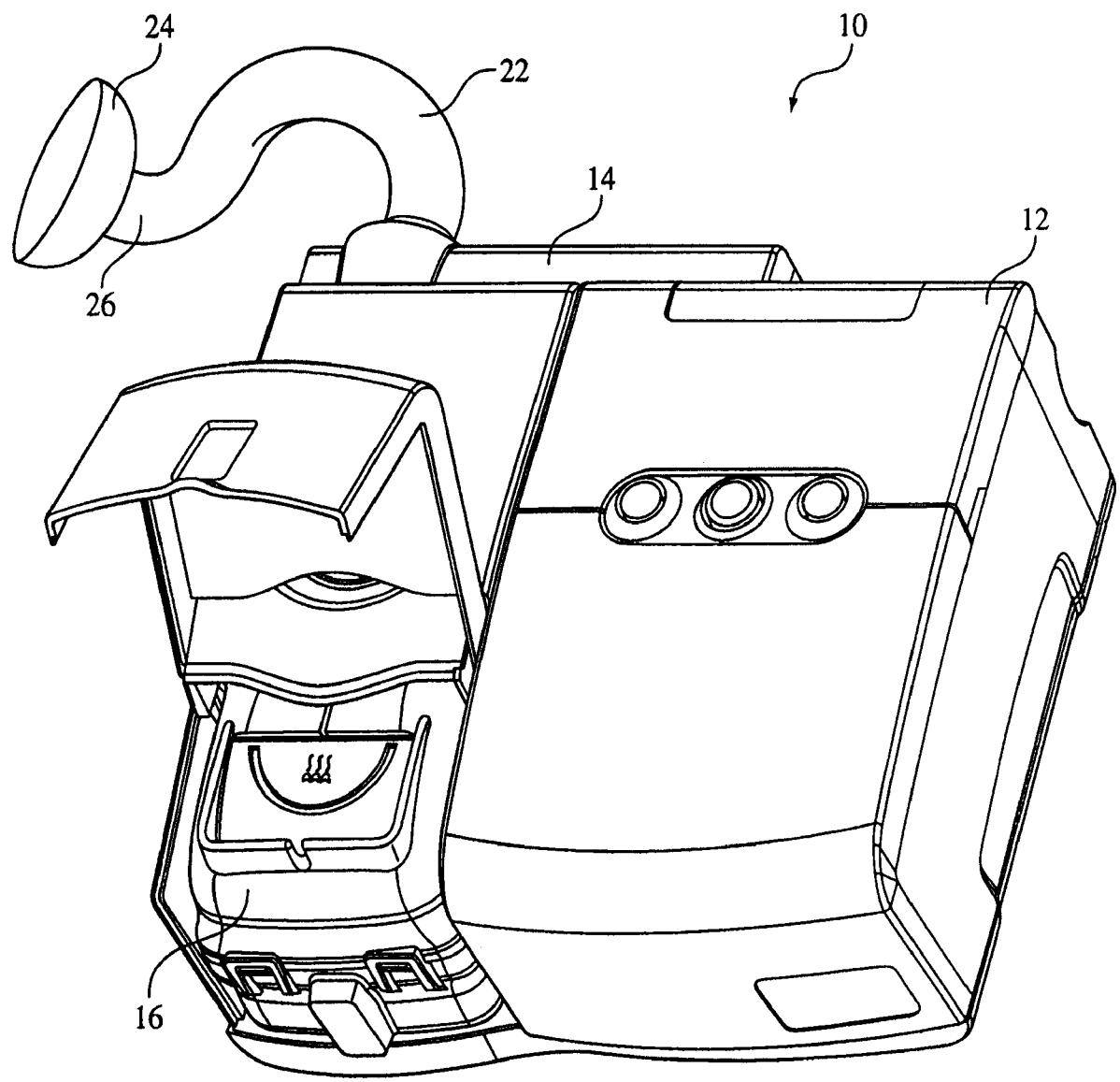
FIG. 1 illustrates a pressure support system, according to one embodiment of the invention.
Figure 1B:
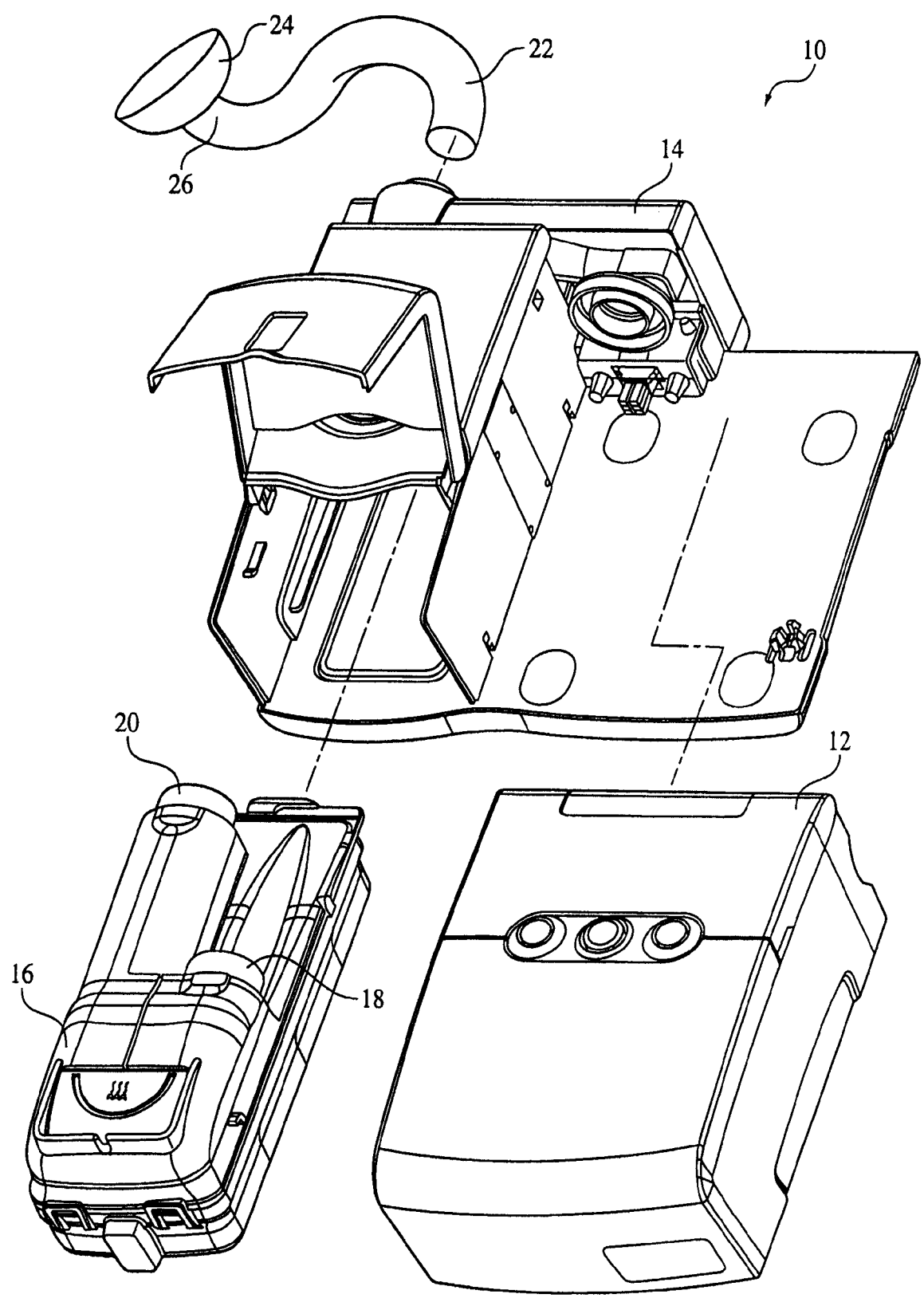

FIGS. 1A and 1B illustrate a pressure support system 10 that provides a pressurized flow of breathable gas to a patient, according to one embodiment of the invention. Pressure support system 10 includes a gas flow generating system 12 that generates the pressurized flow of breathable gas according to a predetermined mode of ventilation. Gas flow generating system 12 is any device that generates a flow of gas for delivery to the airway of a patient. Gas flow generating system 12 may, for example, take the form of a ventilator (invasive, non-invasive, or both), an anesthesia machine, a continuous positive airway pressure (CPAP) device that delivers a flow of gas at a constant pressure, or a variable pressure device that delivers a flow of gas to the patient such that pressure or rate of flow varies. Examples of variable pressure devices include an auto-titrating device that delivers a flow of gas whose pressure varies with the monitored condition of the patient, a proportional assist ventilation (PAV®) device, proportional positive airway pressure (PPAP) device, C-Flex™ device, Bi-Flex™ device, or a BiPAP® device manufactured and distributed by Respironics, Inc. of Pittsburgh, Pa. In a BiPAP device, the pressure provided to the patient varies with the patient's respiratory cycle so that a higher pressure is delivered during inspiration than during expiration, or other pressure support device.

Gas flow generating system 12 is removably placed in communication with a docking assembly 14. Docking assembly 14 receives the pressurized flow of breathable gas generated by gas flow generating system 12 and transmits the pressurized flow of breathable gas to a fluid tank 16. As can be appreciated from FIG. 1B, breathable gas enters tank 16 at a tank inlet 18. The pressurized flow of breathable gas passes through tank 16, and exits the tank at a tank outlet 20. Tank 16 can be filled with a humidity increasing fluid, such as water. It is also know to provide other fluids or mixtures in the tank, such a medicines or scents.

Docking assembly 14 receives the pressurized flow of breathable gas from tank outlet 20, and the pressurized flow of breathable gas flows through docking assembly 14 to a patient circuit 22, that selectively coupled to the docking assembly or the tank outlet. Patient circuit, is any conventional tube that carries the flow of gas to the patient, which can include a single flexible conduit. A patient interface assembly 24 is provided at the distal end of patient circuit 22 to communicate the flow of gas with the airway of the patient. In the illustrated embodiment the patient interface assembly 24 is a mask that covers the nose, mouth, of both. The present invention also contemplates that other devices for communicating a flow of gas to an airway of a patient, such as a mouthpiece, or combination nasal/oral masks, full face mask, tracheal tube, or endotracheal tube are suitable for use as patient interface device 24.

Patient interface assembly 24 may also include a headgear assembly, such as mounting straps or a harness, for removably mounting the patient interface appliance to the patient. In one embodiment, the patient interface assembly may have controls and/or a position sensor mounted thereon, as disclosed in provisional U.S. Patent Application Nos. 60/697,141 and 60/697,140, the contents of which are hereby incorporated by reference into the present application.

In the illustrated embodiment, patient interface assembly 24 and/or patient circuit 22 includes a suitable exhaust port 26 for exhausting gas from these components to ambient atmosphere. Exhaust port 26 may be a passive exhaust port in the form of a continuously open port that imposes a flow restriction on the exhaust gas to permit control of the pressure of gas within patient interface assembly 24. It is to be understood, however, that exhaust port 26 can be an active exhaust port that assumes different configurations to control the exhaust rate. Examples of suitable exhaust ports are taught, for example, in U.S. Pat. Nos. 6,851,425 and 6,615,830, the contents of which are hereby incorporated by reference into the present application.

Figure 2:
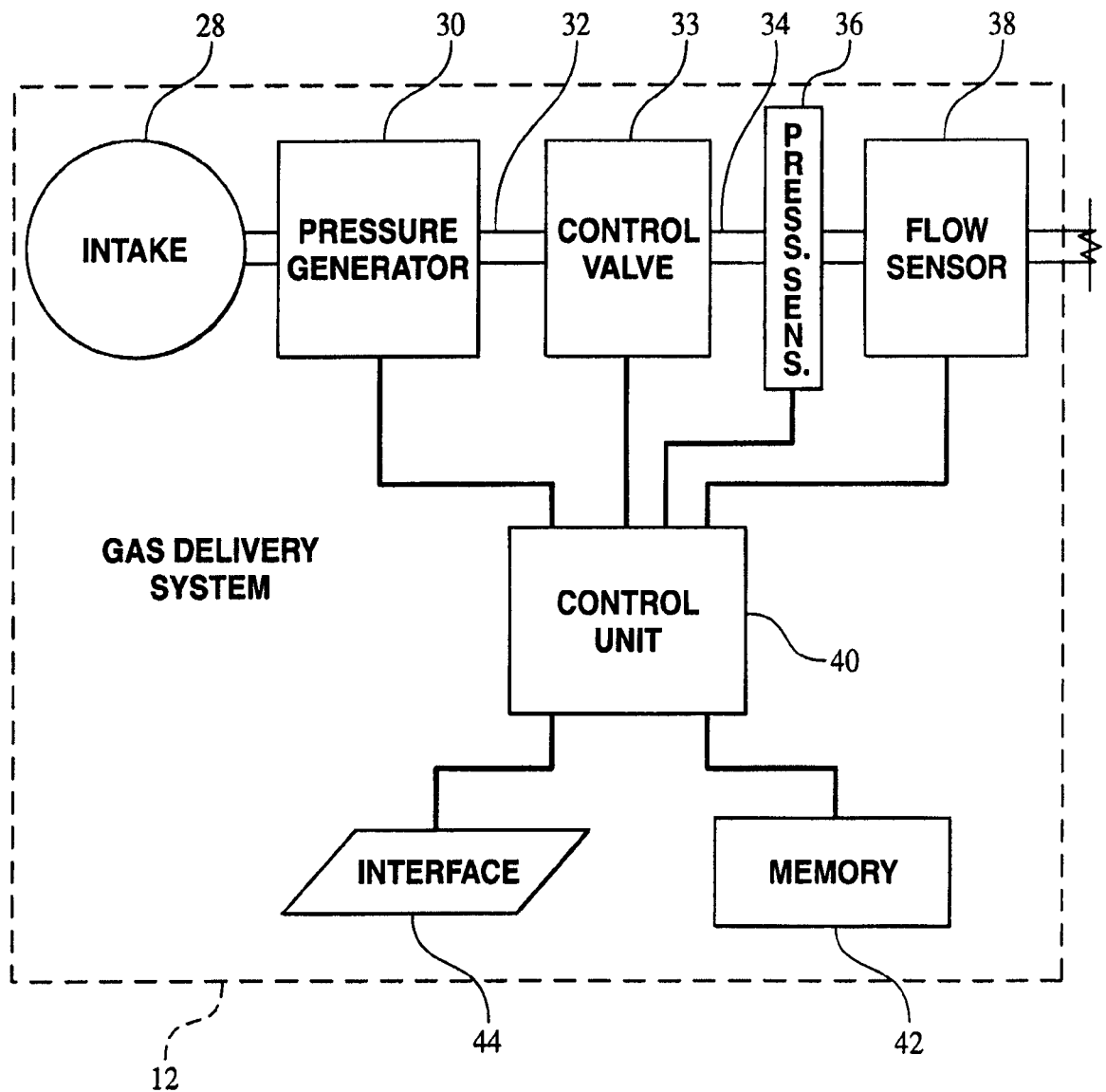
FIG. 2 is a schematic representation of a gas flow generating system included in the pressure support system, in accordance with one embodiment of the invention.

FIG. 2 schematically illustrates an exemplary embodiment of gas flow generating system 12 according to the principles of the present invention. Gas flow generating system 12 includes an intake 28, at which breathable gas from ambient atmosphere (or another gas source, such as a tank of breathable gas) is introduced into gas flow generating system 12. Intake 28 may include a port, a vent, or an opening. In some embodiments, intake 28 may include a filter that filters the breathable gas as it is introduced into circuit 12, and/or a muffler that reduces the noise associated with drawing the breathable gas into the gas flow generating system 12.

As can be appreciated from FIG. 2, a pressure generator 30 receives the breathable gas from intake 28, and elevates the pressure of that gas for delivery to the airway of the patient. Pressure generator 30 may include any device, such as a blower, piston, or bellows that is capable of elevating the pressure of the received breathable gas from intake 28 for delivery to the patient. In one embodiment of the present invention, pressure generator 30 is a blower that is driven at a constant speed during the course of the pressure support treatment to produce a constant pressure or flow rate at its output 32.

In an alternate embodiment to the one shown in FIG. 2, the breathable gas may be received from a gas source other than ambient atmosphere. For example, the gas source may comprise a tank of pressurized gas connected with pressure generator 30. The tank of gas can contain any breathable gas, such as oxygen, air, or other mixture of breathable gas. The present invention also contemplates that a gas source separate from pressure generator 30 need not be used, but instead the pressure generator 30 can itself be defined by a canister or tank of pressurized gas, with the pressure delivered to the patient being controlled by a pressure regulator.

Additionally, in another embodiment, the gas source can be provided in a common housing with the rest of the gas flow generating system 12. In yet another embodiment, the gas source is external to gas flow generating system 12 and provides the pressurized flow of breathable gas so as to constitute a pressure generator, thus eliminating the need for the separate pressure generator 30 within the gas flow generating system 12.

In the illustrated embodiment, gas flow generating system 12 includes a control valve 33. The breathable gas is delivered to control valve 33, with an elevated pressure, downstream of the pressure generator 30. Control valve 33, either alone or in combination with pressure generator 30, controls the final pressure of the breathable gas 34 exiting gas flow generating system 12. Examples of a suitable control valve 33 include at least one valve, such as sleeve or poppet valve, that exhausts gas from the patient circuit as a method of controlling the pressure in the patient circuit. U.S. Pat. No. 5,964,923 to Hete et al., the contents of which are incorporated herein by reference, teaches a dual poppet valve system suitable for use as control valve 33 that exhausts gas to atmosphere and restricts the flow of gas from the pressure generator 30 to the patient.

In embodiments in which pressure generator 30 is a blower that operates at all times at one speed, the control valve 33 alone can be used to control the final pressure and flow rate for the breathable gas 34 output from control valve 33. However, as noted above, the present invention also contemplates controlling the operating speed of pressure generator 30 in combination with control valve 33 to control the final pressure of the pressurized flow of breathable gas delivered to the patient. For example, a pressure or flow rate close to the desired pressure or flow rate can be set by establishing an appropriate operating speed for pressure generator 30 along and by setting the opening in control valve 33 so that the two, operating together, determine the final pressure for the breathable gas 34 exiting gas flow generating system 12.

The pressure of the pressurized flow of breathable gas is measured by a pressure sensor 36. In the embodiment of FIG. 2, pressure sensor 36 is a single sensor unit disposed downstream of pressure generator 30 and control valve 33. However, in other embodiments, pressure sensor 36 may include a single sensor unit disposed elsewhere, such as at an inlet of control valve 33, or at a location downstream from gas flow generating system 12. Alternatively, pressure sensor 36 may include a plurality of sensor units disposed at various locations within gas flow generating system 12. Pressure sensor 36 may include any device, transducer, or devices, capable of measuring the pressure of the pressurized flow of breathable gas generated by gas flow generating system 12.

In the embodiment of FIG. 2, gas flow generating system 12 includes a flow sensor 38. The pressurized flow of breathable gas 34 output from control valve 33 is delivered to flow sensor 38, which measures the instantaneous volume (V) of gas delivered to the patient, and/or the instantaneous flow rate (Q) of such gas to the patient, or both. Flow sensor 38 may include any device suitable for measuring these parameters, such as a spirometer, pneumotach, variable orifice transducer, or other conventional flow transducer. In the illustrated embodiment, flow sensor 38 is provided at a location relatively distant from a patient interface assembly 24. For example, U.S. Pat. No. 6,017,350 to Starr et al., the contents of which are incorporated herein by reference, teaches a quantitative flow member that is located at the patient interface assembly 24. The present invention also contemplates, however, locating flow sensor 38 at any location along patient circuit 22.

As shown, gas flow generating system 12 includes a control unit 40 that controls various operating aspects of gas flow generating system 12. For example, the output of flow sensor 38 and pressure sensor 36 are provided to control unit 40 for processing, if needed, to determine the pressure of the breathable gas, the instantaneous volume (V) of the pressurized flow of breathable gas, and/or the instantaneous flow rate (Q) of the pressurized flow of breathable gas. In some instances, control unit 40 determines the instantaneous volume by integrating the flow rate measured by flow sensor 38. Because, in one embodiment, the flow sensor 38 may be located relatively far from the patient interface assembly 24, in order to determine the actual flow rate of gas to the patient, taking into account, for example, leaks in patient circuit 22 and elsewhere in patient delivery system 10, control unit 40 may receive the output from flow sensor 38 as an estimated flow. The control unit 40 processes this estimated flow information, for example, by performing leak estimation, to determine the actual flow at the patient's airway, as is known to those skilled in the art.

Control unit 40 controls pressure generator 30 and the actuation of control valve 33, thereby controlling the pressure of the pressurized flow of breathable gas generated by the gas flow generating system 12. In one embodiment, control unit 40 comprises a processor that is suitably programmed with an algorithm or algorithms to calculate the pressure to be applied to the patient according to one of any one of various modes of ventilation. In addition, the control unit 40 may be capable of controlling pressure generator 30 and/or control valve 33 based on data received from pressure sensor 36 and/or flow sensor 38 to apply the calculated pressure to the breathable gas within gas flow generating system 12.

In one embodiment of the present invention, the gas flow generating system 12 includes a memory 42 associated with control unit 40 for storing the programming used to perform any of a plurality of modes of ventilation. Memory 42 may also be capable of storing data regarding the operation of the gas flow generating system 12, input commands, alarm thresholds, as well as any other information pertinent to the operation of the gas flow generating system 12, such as measured values of gas flow, volume, pressure, device usage, operating temperatures, and motor speed.

A control interface 44 provides data and commands to control unit 40 of gas flow generating system 12. Control interface 40 may include any device suitable to provide information and/or commands to control unit 40 via a hardwire or wireless connection. Typical examples of control interface 44 may include a keypad, keyboard, touch pad, mouse, microphone, switches, button, dials, or any other devices that allow a user to input information to the gas flow generating system 12. Control interface 44 may also include one or more devices suitable to provide information related to pressure support system 10 to an individual (e.g., a patient, a caregiver, etc.) such as, for example, a screen, a printer, one or more indicator light, a speaker, or other devices that enable the provision information to the individual. For example, treatment reports generated by control unit 40 may be communicated via control interface 44. It should be appreciated that control interface 44 may be located at gas flow generating system 12 or may be located remotely and communicate with control unit 40 via an operative communications link (e.g., hardwired, wireless, etc.). In one embodiment, control interface 44 may be implemented as a Graphical User Interface (GUI) running on a computing terminal that communicates with control unit 40 via a network, or other communications link.

It should be appreciated that the configuration of gas flow generating system 12 shown in FIG. 2 is provided for illustrative purposes, and that alternative configurations of gas flow generating system 12 including some or all of the components shown, as well as additional components, may be implemented. For example, in one embodiment, the final pressure of the breathable gas is not controlled by a control valve, either alone or in combination with pressure generator 30. Instead, gas flow generating system 12 may not include a control valve, and the pressure of the breathable gas is controlled based only on the output of a pressure generator 30. For example, in one embodiment, pressure generator 30 is a blower and control unit 40 (as described in the first embodiment) controls the pressure of the breathable gas delivered to the patient by controlling the motor speed of pressure generator 30. The present invention contemplates implementing the pressure of the breathable gas as measured by pressure sensor 36 and a speed monitor for the blower motor to provide feedback data to control unit 40 for controlling the operation of pressure generator 30.

In addition, gas flow generating system 12 (as shown in either of FIG. 1 or 2) and related components may include other conventional devices and components, such as a humidifier, heater, bacteria filter, temperature sensor, humidity sensor, and a gas sensor (e.g., a capnometer), that filter, measure, monitor, and analyze the flow of gas to or from the patient.

Figure 3:
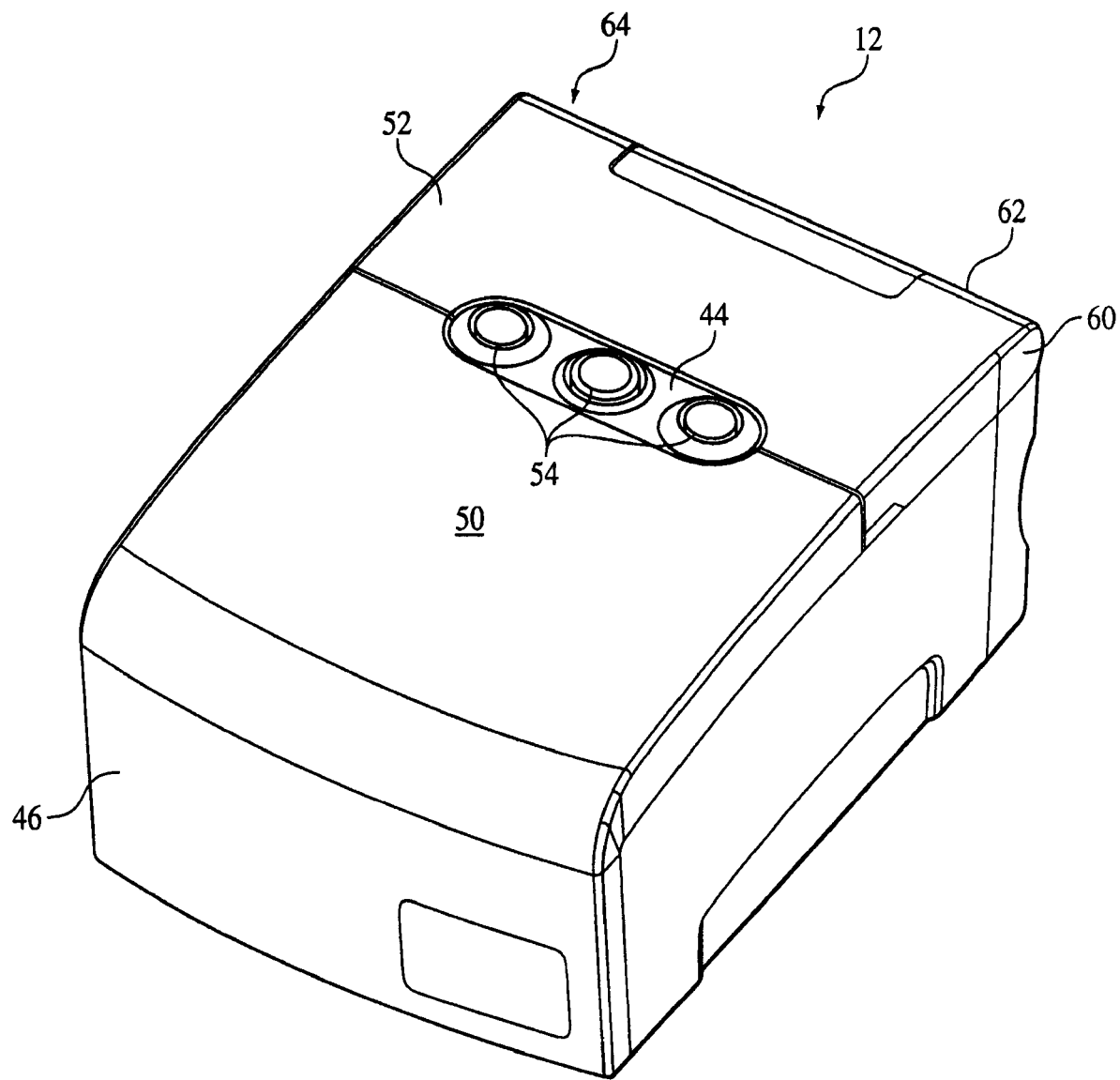
FIG. 3 is a perspective view of the gas flow generating system, according to one embodiment of the invention.
Figure 4:
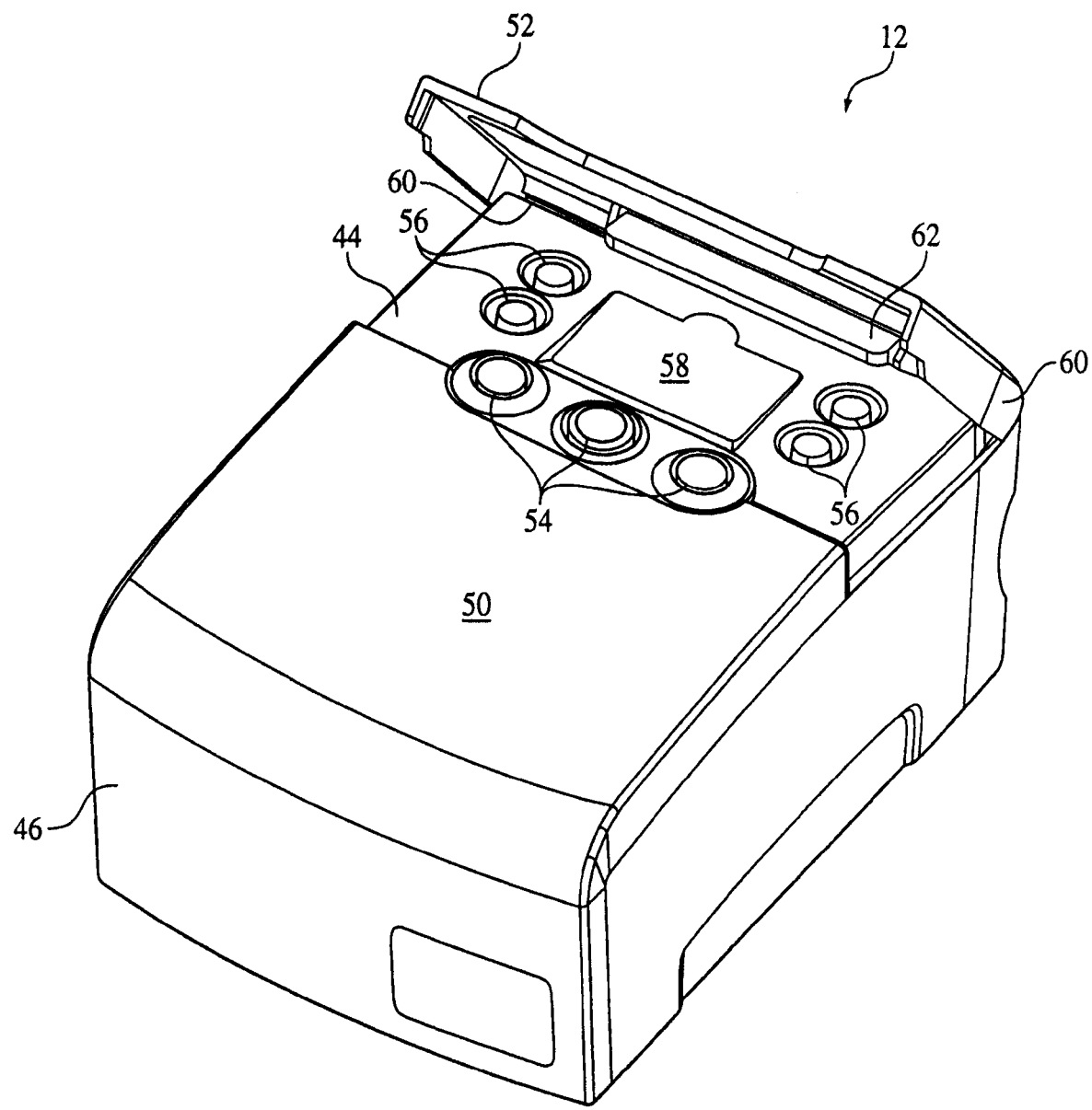
FIG. 4 is a perspective view that illustrates the gas flow generating system according to one embodiment of the invention.

FIG. 3 illustrates a perspective view of gas flow generating system 12, in accordance with one embodiment of the invention. Gas flow generating system 12 includes a housing 46. As can be seen in FIG. 3, control interface 44 is provided on a top side 50 of housing 46. Control interface 44 is partially covered by a control interface cover 52. When cover 52 is in the closed position, illustrated in FIG. 3, primary controls 54 are accessible to an individual. However, when cover 52 is opened, as shown in FIG. 4, ancillary controls 56 also become accessible to the individual, in addition to primary controls 54. In the embodiment shown, opening cover 52 uncovers a display screen 58.

In an exemplary embodiment of the present invention, primary controls 54 enable an individual to control one or more aspects of the operation of gas flow generating system 12 such as, for example, a power on/off function, a pressure ramp function, a C-Flex™ function as known in the art, or another aspect of operation. Uncovering ancillary controls 56 enables the individual to control one or more additional aspects of the operation of gas flow generating system 12 via ancillary controls 56, and to view display screen 58. For instance, display screen 58 may display one or more of a plurality of selectable menus, and the menus can be navigated via ancillary controls 56. In another embodiment, display screen 58 may be a touch sensitive screen that not only functions as a display, but also replaces the function provided by buttons or other controls 56.

As can be appreciated from FIGS. 3 and 4, control interface cover 52 opens and closes by pivoting about hinges 60 mounted on a corner 62 of housing 46 between top side 50 of housing 46 and a rear side 64 of housing 46. In one embodiment, hinges 60 are break-away hinges that allow the control interface cover 52 to break off from housing 46 if hinges 60 are over-stressed (e.g., due to a drop, etc.), and be re-attached without permanently damaging control interface cover, housing 46, or hinges 60. It will be appreciated that control interface cover 52 may cover and uncover control interface 44 via a mechanism other than hinges 60. For instance, in one embodiment, control interface cover 52 includes guides that slide in a track formed in housing 46 to slide control interface cover 52 into and out of position over control interface 44. In another embodiment, control interface cover 52 is detached entirely from housing 46 to uncover control interface 44, and is re-attached to housing 46 to cover control interface 44.

Figure 5:
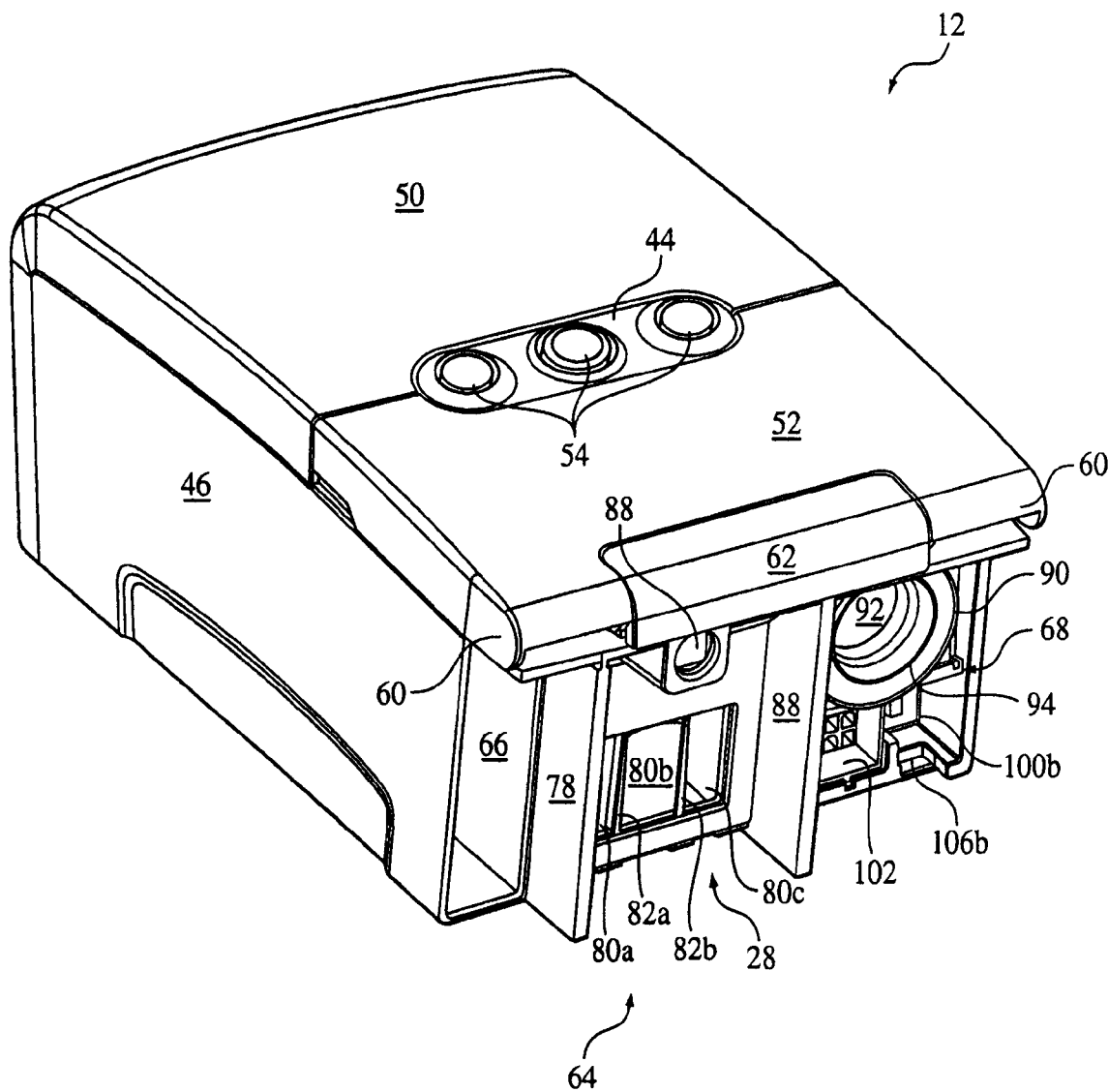
FIG. 5 is a perspective view showing a rear side of the gas flow generating system, in accordance with one embodiment of the invention.
Figure 6:
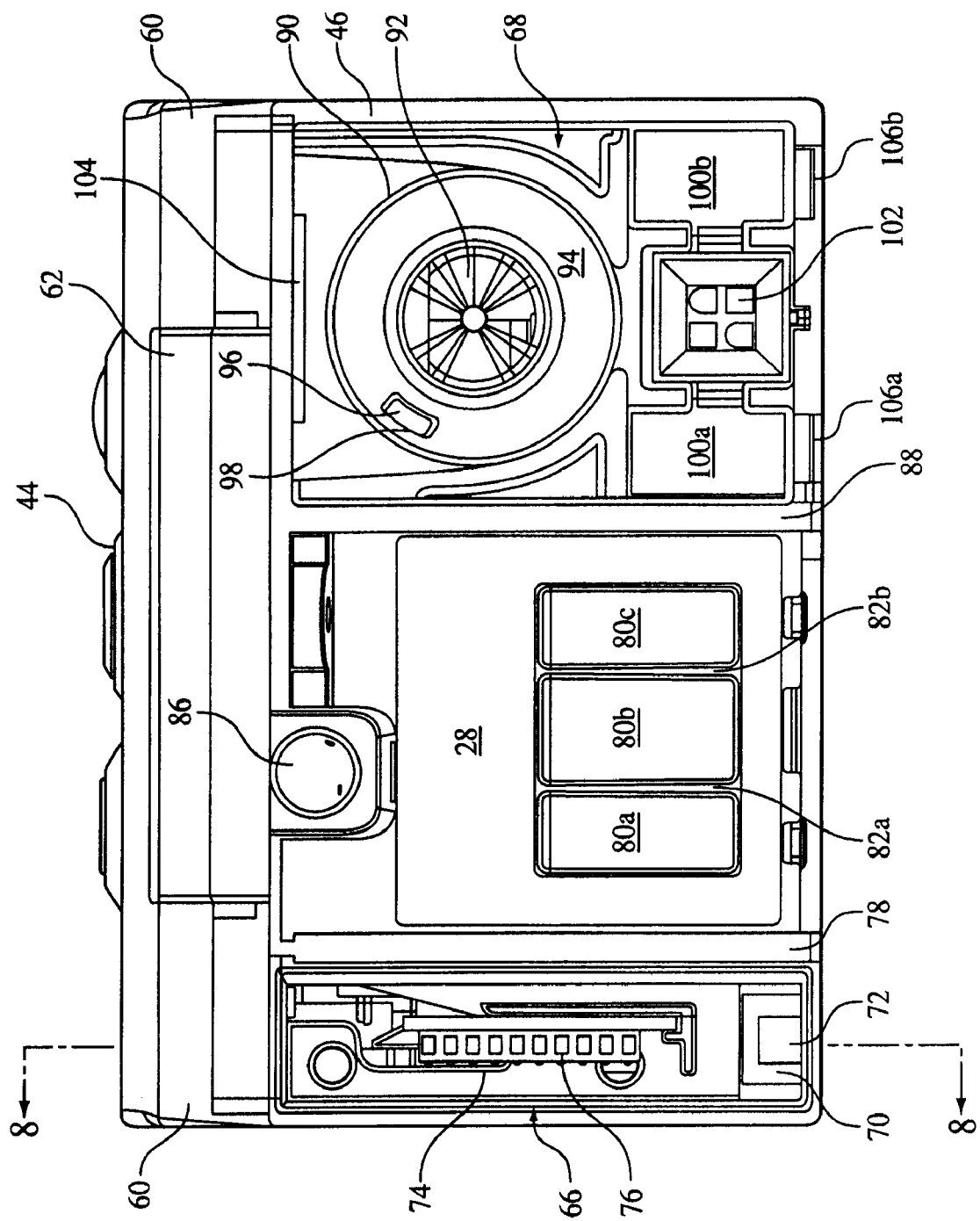
FIG. 6 is a rear elevational view of the gas flow generating system, according to one embodiment of the invention.

FIG. 5 is a rear perspective view of gas flow generating system 12 according to one embodiment of the invention. At rear side 64 of housing 46 a modular accessory port 66, intake 28, and a docking interface 68 are formed. FIG. 6 is a rear plan view that shows modular accessory port 66 including a tab engaging member 70 that forms a tab opening 72. Modular accessory port also includes an accessory interface 74, illustrated in FIG. 6 as including an electronic parallel port 76. A partition 78 separates modular accessory port 66 from intake 28. At intake 28, housing 46 forms a recess to receive an intake module, as will be described below. A plurality of intake openings 80 (illustrated as intake openings 80a-80c) are formed in housing 46 at intake 28, the intake openings 80 being separated by one or more intake partitions 82 (illustrated as intake partitions 82a and 82b).

One or more intake module engaging slots (not shown) are also provided on housing 46 at intake 28 on an underside of housing 46. Positioned just above intake 28, a delivery system power connection 86 provides an interface at which power may be provided to gas flow generating system 12 from an external power source. A partition 88 separates intake 28 from docking interface 68. Docking interface 68 includes a delivery system outlet 90 that extends from housing 46. Delivery system outlet 90 includes outlet opening 92 defined by an annular lip 94. A pressure conduit 96 is formed in delivery system outlet 90, and communicates an opening 98 with pressure sensor 36 (not shown in FIG. 6) within gas flow generating system 12. In one embodiment, delivery system outlet 90 is composed of a different material than housing 46 (which may be composed of a hard plastic or composite material), which is softer and more pliable than housing 46. For example, silicon or another pliable material, may be used.

One or more docking port recesses 100 (shown as docking port recesses 100a and 100b) are formed in housing 46 at docking interface 68. Between docking port recesses 100, a connector 102 is provided. A primary docking port catch 104 is formed by housing 46 at one inner surface of docking interface 68, and, at a first side of each of docking port recesses 100a and 100b, secondary docking port catches 106a and 106b are formed in housing 46.

Figure 7:
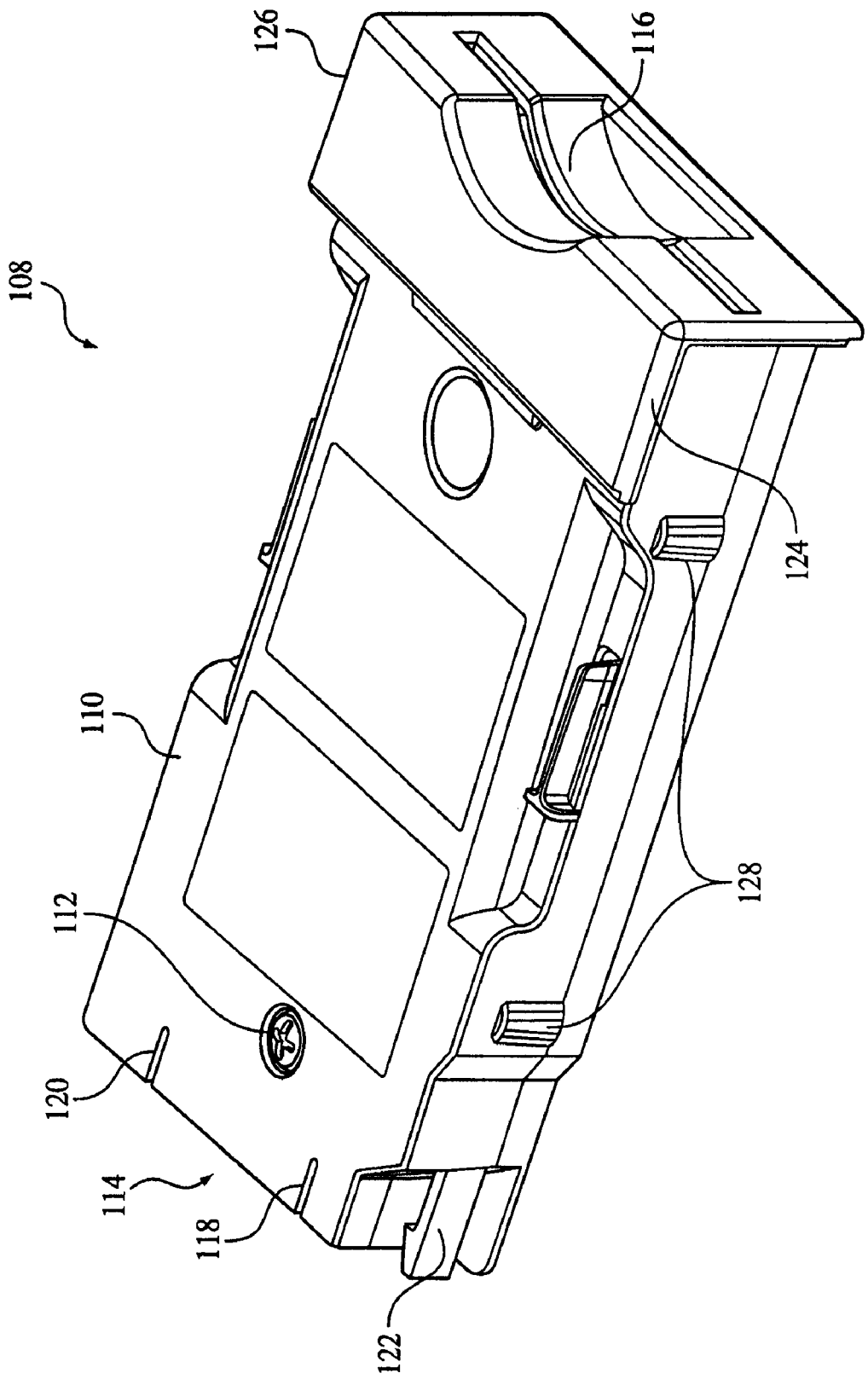
FIG. 7 illustrates a modular accessory, in accordance with one embodiment of the invention.

FIG. 7 is a perspective view of a modular accessory 108, according to one embodiment of the invention. Modular accessory 108 is substantially encased by a modular accessory housing 110 that is held together by a fastener 112. Modular accessory 108 includes a delivery system interface 114 at a first end of modular accessory housing 110, and a communication unit 116 at a second end. At delivery system interface 114, a first guide groove 118 and a second guide groove 120 are formed in modular accessory housing 110. A barbed tab 122 is also formed at the first end of modular accessory housing 110, on a first side of modular accessory 108. At the second end of modular accessory 108, modular accessory housing 110 forms a first overhang 124 at the left side of modular accessory 108, and a second overhang 126 at the right side of modular accessory 108. At each side of modular accessory 108, guide protrusions 128 are formed on modular accessory housing 110.

Figure 8:
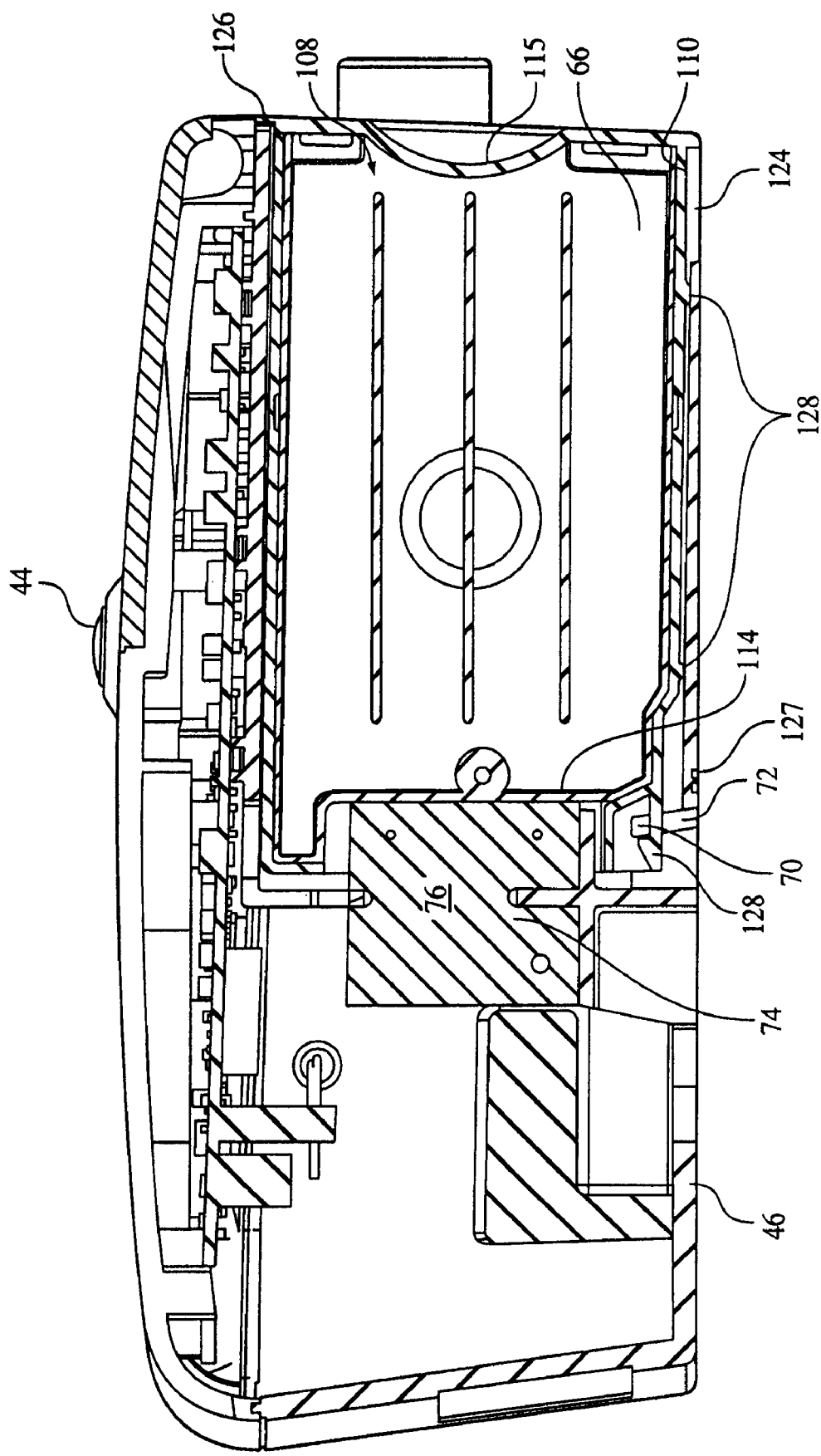
FIG. 8 is a sectional view of the gas flow generating system, taken along section lines 8-8 shown in FIG. 6, with the modular accessory installed in the gas flow generating system, according to one embodiment of the invention.

In one embodiment of the invention, modular accessory housing 110 is adapted to interface with gas flow generating system 12 via modular accessory port 66 of housing 46. FIG. 8 illustrates side elevation of gas flow generating system 12 along section line 8-8 that illustrates modular accessory 108 disposed within modular accessory port 66. Delivery system interface 114 connects with accessory interface 74 to enable modular accessory 108 to interface with gas flow generating system 12. In one embodiment of the invention, delivery system interface 12 is a male electronic parallel port held within modular accessory housing 110 that plugs into female electronic parallel port 76 (seen best in FIG. 6) when modular accessory 108 is inserted into modular accessory port 66.

In one embodiment, connecting interfaces 13 and 35 forms an operative link between communication unit 116 and control unit 40. Via this operative link, information may be transmitted between from communication unit 116 to control unit 40, and from control unit 40 to communication unit 116. When modular accessory 108 is placed within modular accessory port 66, guide protrusions 128 contact an inner surface of modular accessory port 66 to position modular accessory 108 in modular accessory port 66 so that guide grooves 23 and 25 (see FIG. 7; not shown in FIG. 8) can guide delivery system interface 114 into connection with accessory interface 74. As modular accessory 108 is positioned within modular accessory port 66, barbed tab 122 slides through tab opening 72, and becomes engaged with a member 70 to secure modular accessory 108 in place within modular accessory port 66. As barbed tab 122 becomes engaged with member 70, overhangs 124 and 126 act as stops to prevent modular accessory 108 from being inserted too far into modular accessory port 66. Overhangs 126 and 126 also define a corner of housing 46, so that the side and back of the housing are each presented as a relatively flat surface, thereby enhancing the aesthetics of the housing when modular accessory 108 is coupled to the housing.

To remove modular accessory 108 from modular accessory port 66, barbed tab 122 is released from member 70 and modular accessory 108 is slid out of modular accessory port 66. To release barbed tab 122 from member 70, an individual depresses a depressible surface 127, which actuates member 70 to position tab opening 72 upwards (in the view shown) to disengage barbed tab 122 from member 70. The disengagement of tab 122 from member 70 enables tab 122 to be retracted back through tab opening 72 as modular accessory 108 is removed from modular accessory port 66.

In one embodiment of the invention, the information transmitted from control unit 40 of gas flow generating system 12 to communication unit 116 may include information related to the pressurized flow of breathable gas, such as an amount of breathable gas delivered to the patient, an amount of time during which the pressurized flow of breathable gas has been delivered to the patient, the flow rate of the breathable gas, the pressure of the breathable gas, and/or other information related to the pressurized flow of breathable gas. In one embodiment, the information transmitted from control unit 40 to communication unit 116 includes information related to a malfunction of gas flow generating system 12. In another embodiment, the information includes information related to operations settings being stored by, or implemented in, gas flow generating system 12.

In the embodiment of modular accessory 108 illustrated in FIGS. 7 and 8, communication unit 116 includes a writable electronic media drive that is capable of outputting some or all of the information transmitted to communication unit 116 from control unit 40 by writing the information to a writeable electronic media. An example of a smart card as such a media for use in transmitting information to or receiving information from a pressure support system is disclosed in U.S. patent application Ser. No. 09/698,743, the contents of which are incorporated herein by reference. A corresponding PCT application from this US application was published as PCT Publication No. WO 01/32069.

In another embodiment, communication unit 116 includes a connection to a network, such as a Local Area Network (LAN), Wide Area Network (WAN), the Internet, or another network. In this embodiment, the information transmitted to communication unit 116 is output from communication unit 116 to the network. In another embodiment of the invention, communication unit 116 includes a wireless transmitter, and the information transmitted to communication unit 116 from control unit 40 is output from communication unit 116 by wireless transmission.

In one embodiment of the invention, the information transmitted from communication unit 116 to control unit 40 includes information related to a communication unit type of communication unit 116. For example, in an embodiment in which communication unit 116 includes a network connection, communication unit 116 may include one or more capabilities not found in an embodiment in which communication unit includes a writable electronic media drive. Further, information may need to be formatted differently for transmission from control unit 40 to communication unit 116 based on the communication unit type. Thus, transmitting information from communication unit 116 to control unit 40 may enhance subsequent interaction between communication unit 116 and control unit 40.

It is to be understood that accessory port 66 and the associated connection terminals provide a means for enabling a variety of devices to interface with the gas flow delivery system. For example, the present invention contemplates a battery pack can provided in accessory port 66.

Figure 9:
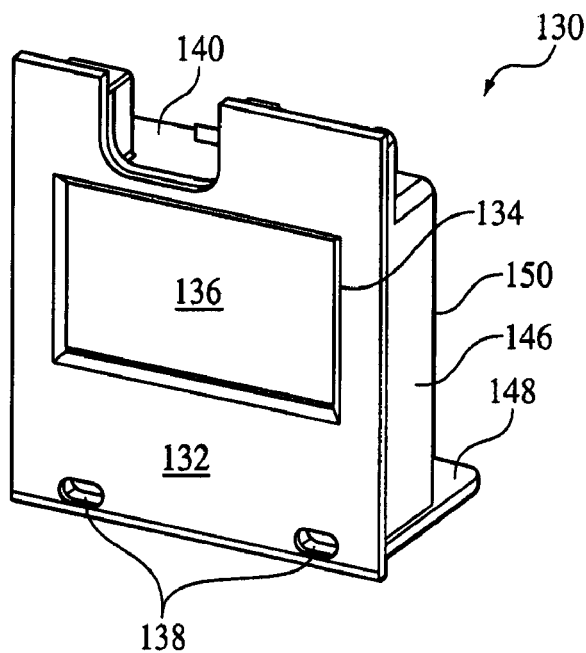
FIG. 9 illustrates an input module, in accordance with one embodiment of the invention.

FIG. 9 illustrates a perspective view of an intake module 130, in accordance with one embodiment of the present invention. Intake module 130 includes an outer plate 132 that is oriented essentially as a vertical plane when intake module 130 is disposed in intake 28. Plate 132 forms a primary opening 134, in which a filter media 136 is disposed. One or more secondary openings 138 are also formed in plate 132. A cut-out 140 is formed by plate 132 to accommodate delivery system power connection 86 when intake module 130 is installed at intake 28.

Figure 10:
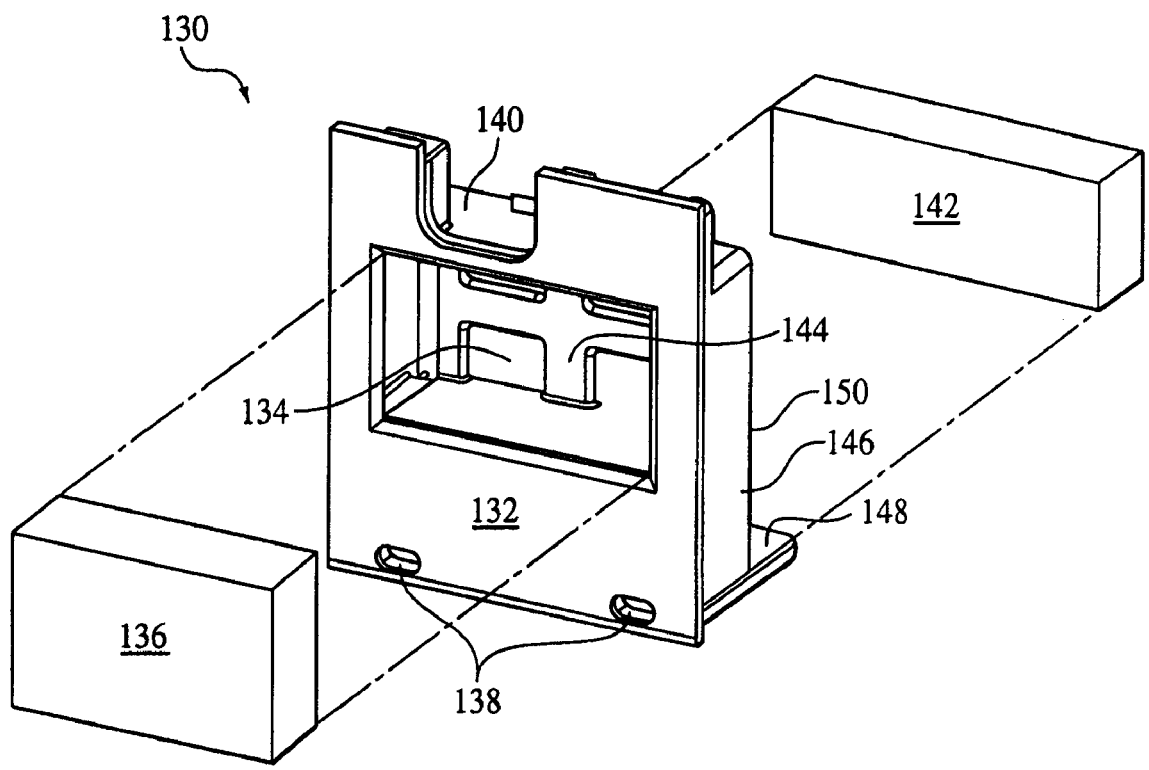
FIG. 10 is an exploded view of the input module, according to one embodiment of the invention.

Referring to FIG. 10, which shows a view of intake module 130 with filter media 136 and an acoustic foam 142 exploded from intake module 130. In one embodiment of the invention, filtering element 136 is composed of an open cell foam an includes a layer of an ultrafine filtering material to filter smaller particles. As can be seen in FIG. 10, primary opening 134 in plate 132 communicates with a filter stop 144 that holds filter media 136 in place. Acoustic foam 142 sits in a sound trap (not shown) formed underneath primary opening 134. A ridge 146 is formed at the periphery of plate 132, and extends substantially perpendicular to plate 132, back into gas flow generating system 12 when intake module 130 is disposed at intake 28. A lower portion 148 of ridge 146 extends further away from plate 132 than other portions of ridge 146, and one or more tabs (not shown) are formed on a bottom surface (in the orientation shown in FIGS. 9 and 10) of lower portion 148.

To install intake module 130 at intake 28, ridge 146 is positioned within intake 28 such that side portions 150 of ridge 146 engage partitions 78 and 88, and act as guides as intake module 130 is placed within intake 28. Lower portion 148 of ridge 146 fits slides along housing 46 such that the tabs formed on lower portion 148 slide into, and engage the intake module engaging slots located under housing 46, thereby securing intake module 130 within intake 28. Air is introduced into gas delivery device 12 via intake module 130. The air enters intake module 130 at primary opening 134, passes through filter media 136 and acoustic foam 142, and enters housing 46 at intake openings 80. As the air is introduced to gas flow generating system 12, filtering element 136 filters the air, and intake openings 80, intake partitions 82, and the sound trap that holds acoustic foam 142 (as well as acoustic foam 142) serve to muffle the sound of the air entering housing 46.

Figure 11:
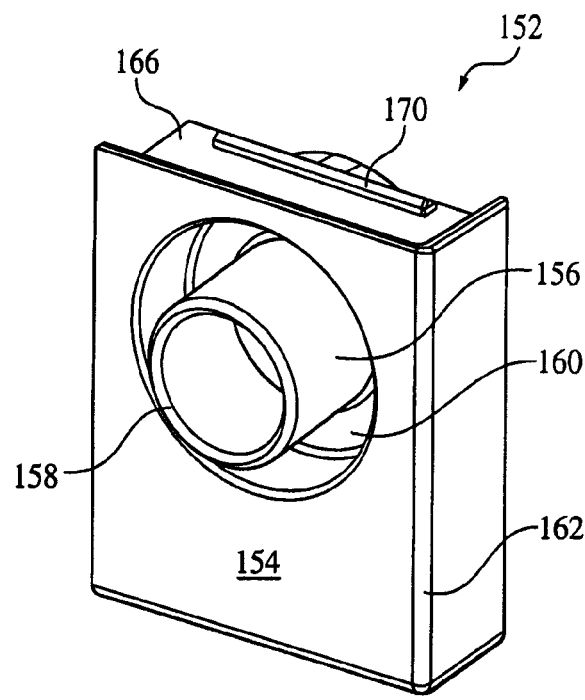
FIG. 11 illustrates a removable outlet port, in accordance with one embodiment of the invention.

FIG. 11 shows a removable outlet port 152 that can be removably coupled to docking interface 68. Removable outlet port 152 includes an outer plate 154 that is oriented essentially as a vertical plane when removable outlet port 152 is coupled to docking interface 68. A circuit interface 156 is formed in plate 154 that enables patient circuit 22 to be coupled to removable outlet port 152. Circuit interface 156 includes an outlet conduit 158 that extends out of removable outlet port 152, surrounded by an annular groove 160 formed in plate 154. On a first edge 162 of removable outlet port 152, plate 154 makes roughly a right angle, and wraps around removable outlet port 152. Thus, removable outlet port 152 defines a corner of housing 46 so that the side and back of the housing are each presented as a relatively flat surface, thereby enhancing the aesthetics of the housing when the removable outlet port is coupled to the housing.

Figure 12:
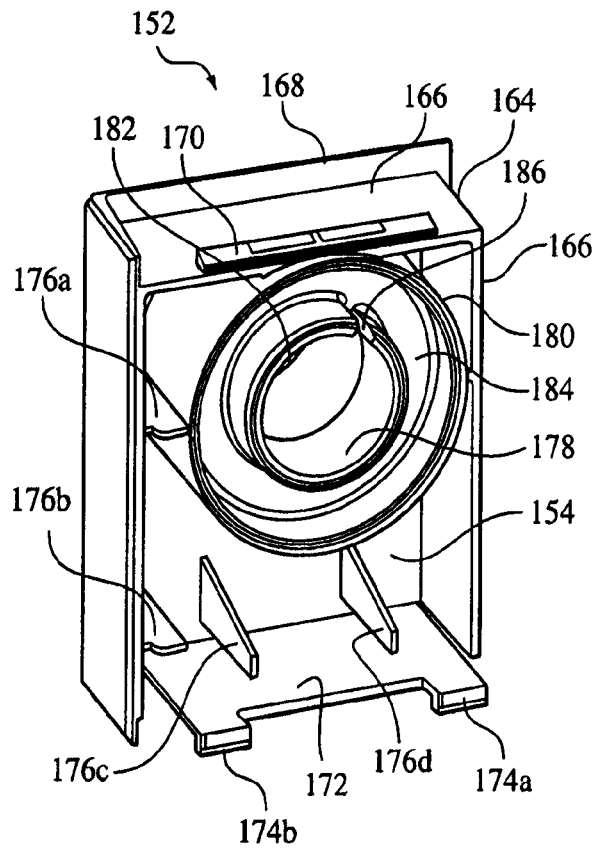
FIG. 12 is a reverse view of the removable outlet port, according to one embodiment of the invention.

As can be seen in FIG. 12, which includes a reverse view of removable outlet port 152 from FIG. 11, near a second edge 164 of plate 154, on an opposite side of plate 154 from circuit interface 156, a ridge 166 is formed that extends perpendicular to the plane of plate 154. Near an upper (in the orientation shown in FIG. 12) edge 168 of plate 154, ridge 166 turns at an approximately 90 degree angle and runs parallel to upper edge 168 of plate 154 until ridge 166 meets the plate 154 at first edge 162 of removable outlet port 152. On an upper surface of ridge 166, a protrusion 170 with a triangular profile is formed.

As is illustrated in FIG. 12, a planar tab member 172 extends from plate 154 in a substantially perpendicular direction from plate 154. At an edge of tab member 172 opposite from plate 154 barbed tabs 174 (illustrated as barbed tabs 174a and 174b) are formed. A plurality of support struts 176 (illustrated as support struts 176a-176d) are formed on plate 154 and tab member 172 to reinforce tab member 172 when tab member 172 is flexed during insertion.

Opposite from circuit interface 156, an outlet interface 178 is formed. Outlet interface 178 interfaces with delivery system outlet 90. Outlet interface 178 includes an outer annular ridge 180 that rises out of plate 154. The inner diameter of outer annular ridge 180 is slightly smaller than the outer diameter of annular lip 94 of delivery system outlet 90. An inner annular ridge 182 is formed coaxially with outer annular ridge 180. The diameter of inner annular ridge 182 corresponds substantially to the diameter of outlet opening 92. An annular groove 184 is formed in between annular ridges 180 and 182. A gap 186 is formed in inner annular ridge 182.

To couple removable outlet port 152 to docking interface 68, removable outlet port 152 is positioned such that barbed tabs 174 are positioned to engage secondary docking port catches 106a and 106b. Then removable outlet port 152 is pivoted about these engaged components until protrusion 170 clears primary catch 104, and becomes engaged therewith, securing removable outlet port 152 within docking interface 68. Coupling removable outlet port 152 to docking interface 68 in this manner causes annular ridges 180 and 182 to engage annular lip 94 of delivery system outlet 90. Since, in one embodiment, annular lip 94 is formed of a compliant material, such as silicon or another compliant material, annular ridges 180 and 182 press into annular lip 94 and create a seal therebetween. This enables air passing out of gas flow generating system 12 at delivery system outlet 90 through outlet opening 92 to be transmitted through circuit interface 156 without substantial loss. Annular ridges 180 and 182 engage annular lip 94 such that opening 98 of pressure conduit 96 is received in annular groove 184. Gap 186 enables opening 98 to communicate with outlet opening 92 such that air may be transmitted between the openings 98 and 92.

Removable outlet port 152 is removed from docking interface 68 by applying a pressure on tab member 172 until tabs 174 disengage from catches 75, and removable outlet port 152 is freed from the attachment to housing 46. Removable outlet port 152 may be attached to gas flow generating system 12 in instances where a patient desires to receive a pressurized flow of breathable gas without using docking assembly 14. The patient uses removable outlet port 152 by coupling removable outlet port 152 to docking interface 68, as described above, and coupling patient circuit 22 to circuit interface 156, so that the pressurized flow of breathable gas may be received via patient circuit 22 and patient interface assembly 24.

Figure 13:
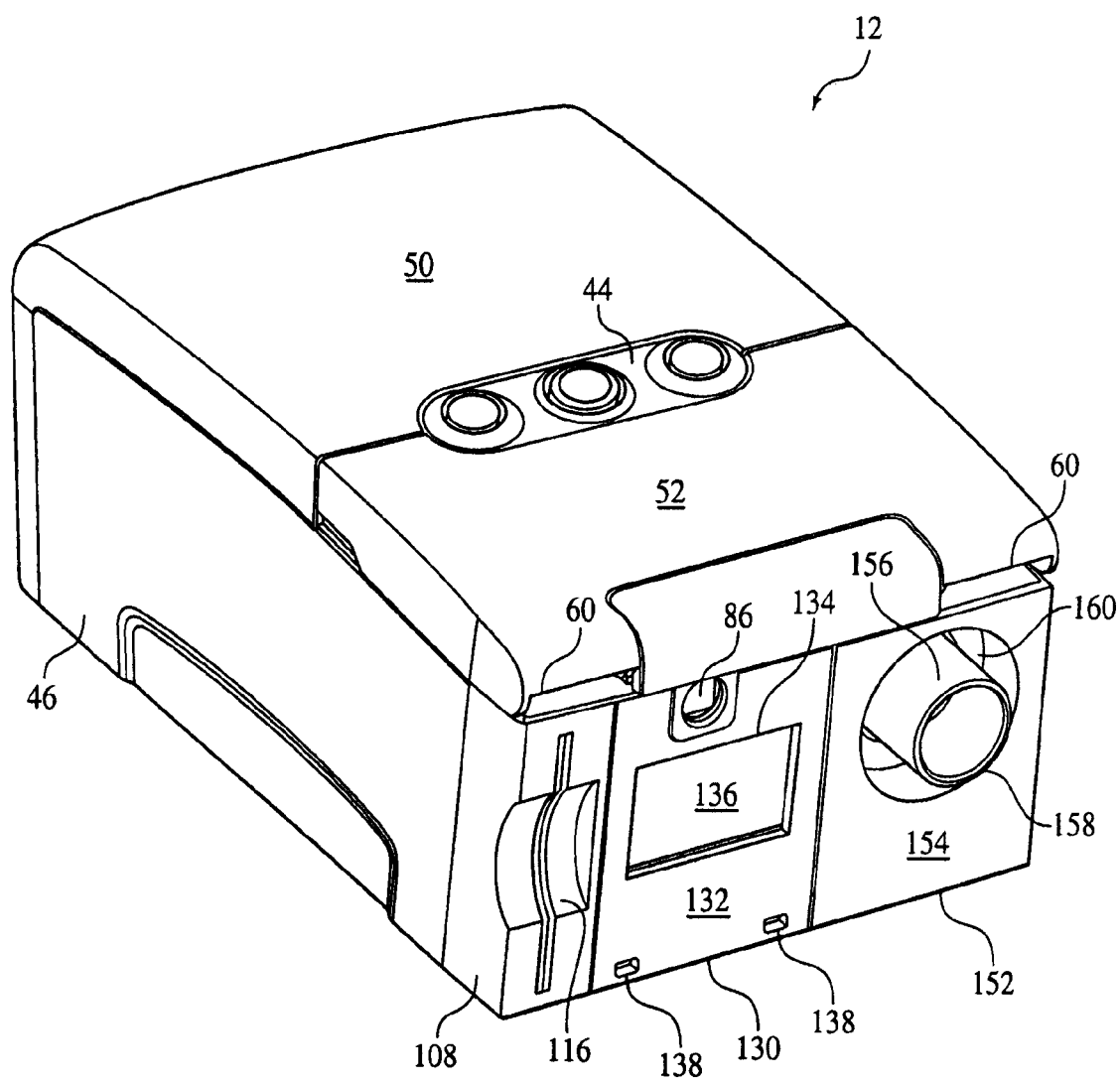
FIG. 13 is a rear perspective view of the gas flow generating system, in which the modular accessory, the input module, and the removable outlet port have been installed, in accordance with one embodiment of the invention.

FIG. 13 is a rear perspective of gas flow generating system 12 according to an embodiment of the invention. Unlike the view illustrated in FIG. 5, in FIG. 13, modular accessory 108, intake module 130, and removable outlet port 152 are removably installed on housing 46 at modular accessory port 66, intake 28, and docking interface 68, respectively. This figures dramatically illustrates how the exterior wall of the housing are formed, in part, by modular accessory 108, intake module 130, and removable outlet port 152, so that when the system is fully assembled, it has a smooth, clean appearance.

Figure 14:
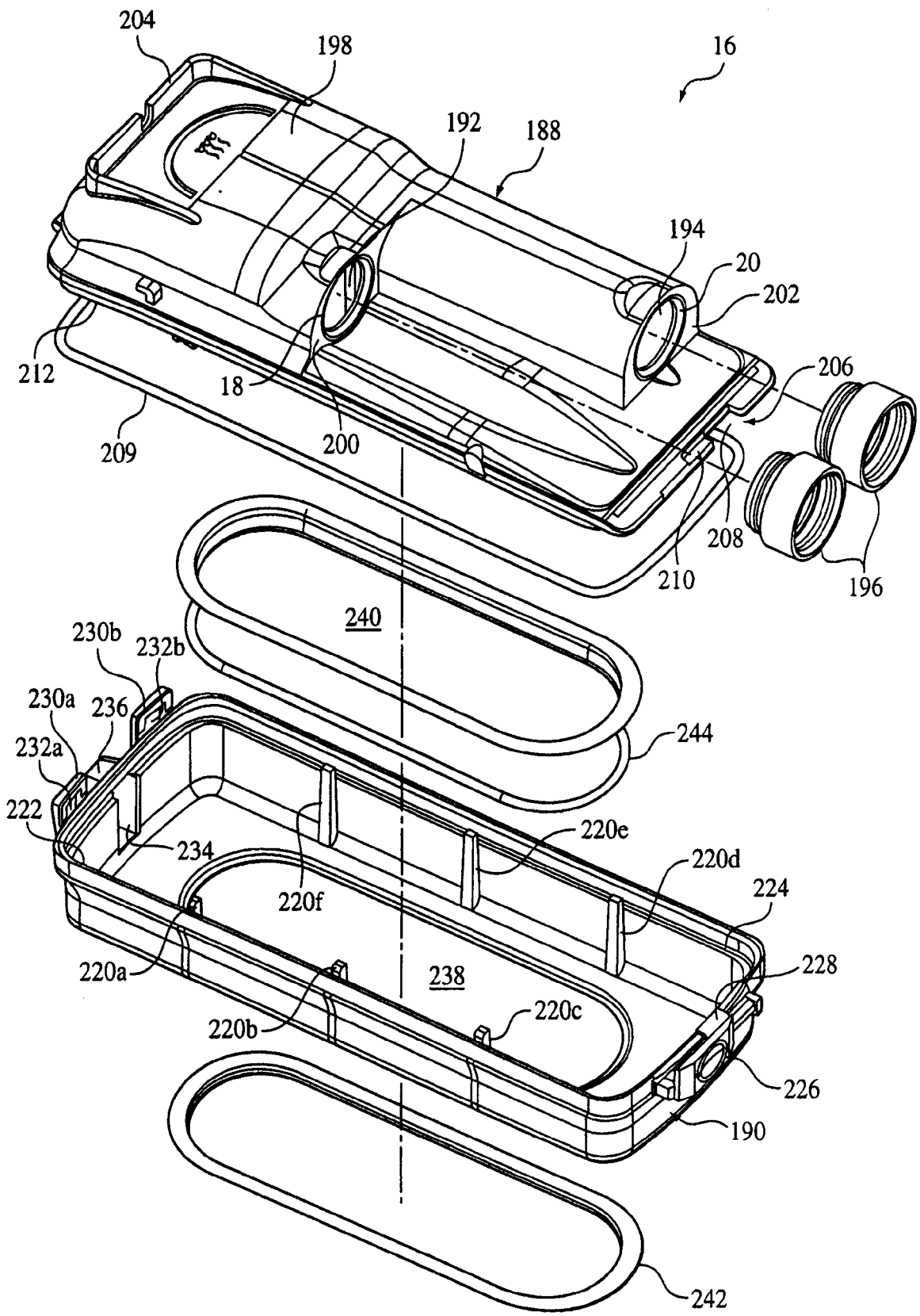
FIG. 14 is an exploded view of a tank included in the pressure support system, according to one embodiment of the invention.

As can be seen in the exploded view of tank 16 shown in FIG. 14, tank 16 includes an upper tank housing 188 and a lower tank housing 190 that are removably coupled to each other. In one embodiment, tank housings 188 and 190 are formed from a substantially hard material, such as a rigid plastic and/or composite material. A tank inlet opening 192 and a tank outlet opening 194 are formed in upper tank housing 188, oriented toward a rear end of tank 16. A tank seal 196 is installed at each of tank inlet opening 192 and tank outlet opening 194 to form tank inlet 18 and tank outlet 20, respectively. Tank seals 196 form short conduits, and are composed of a soft, pliable material, such as silicon, or another pliable material.

As is illustrated in FIG. 14, upper tank housing 188 includes an elevated portion 198 situated substantially to a front end of tank 16, the front end being opposite from the rear end of tank 16. Toward a first side of tank 16, at a transition surface 200 between elevated portion 198 and the rest of upper tank housing 188, tank inlet opening 192 is formed. Transition surface 200 is a substantially vertical wall that joins elevated portion 198 with the rest of upper tank housing 188. Toward a second side of tank 16, opposite from the first side of tank 16, elevated portion 198 extends from the rear end of upper tank housing 188 almost all the way to the front end of upper tank housing 188. At a transition surface 202, formed in upper tank housing 188 toward the second side of tank 16, tank outlet opening 194 is formed. At the front end of upper tank housing 188, on an upper surface of elevated portion 198, a handle ridge 204 is formed. At an edge of upper tank housing 188, on the rear end of tank 16, a catch engaging region 206 includes a cutout 208 and a ledge 210. At an edge of upper tank housing 188, on the front end of tank 16, a pair of tabbed protrusions (not shown) are formed. An upper tank housing rim 212 is formed around the edge of upper tank housing 188.

Figure 15:
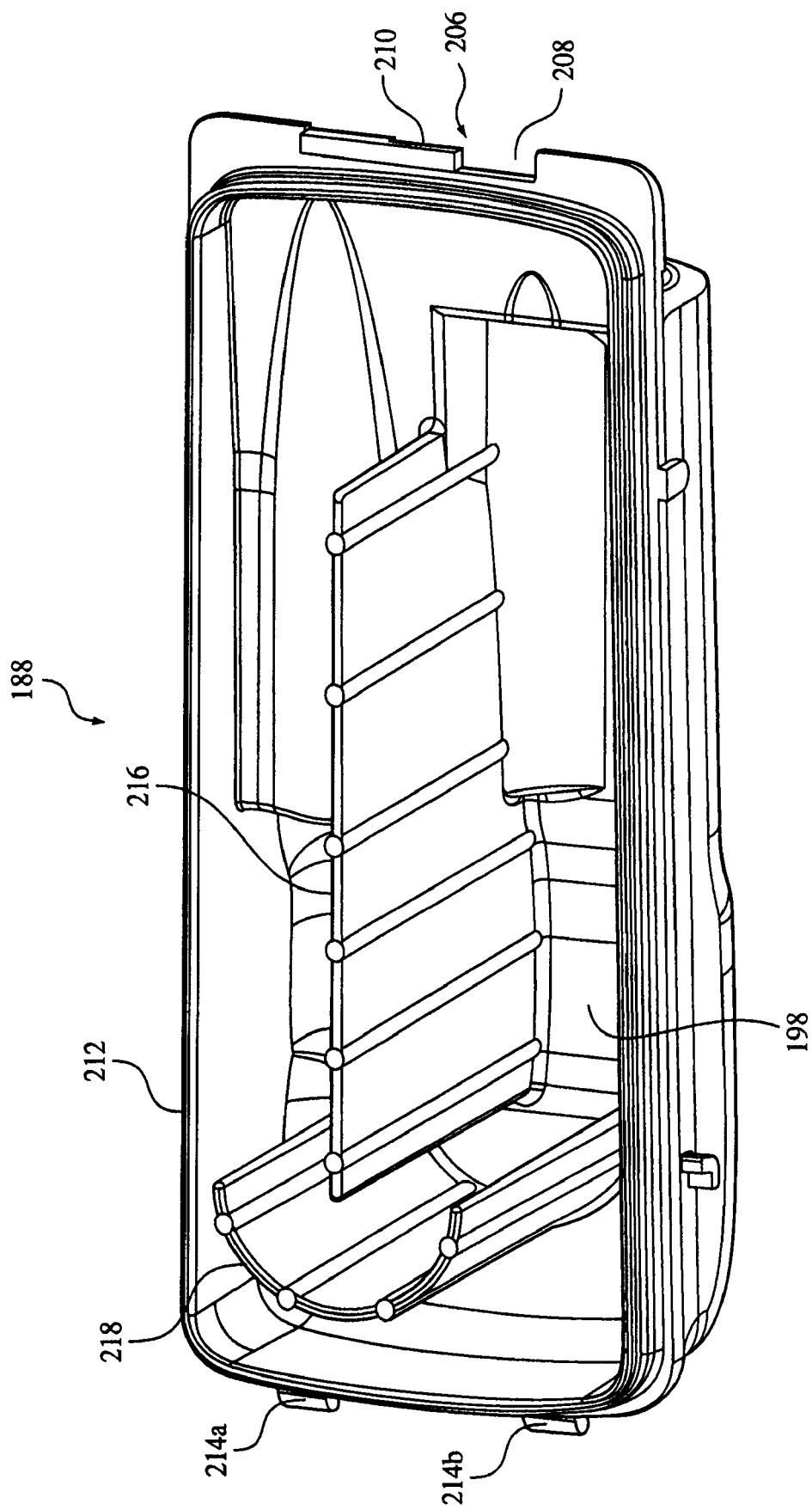
FIG. 15 illustrates an upper tank housing included in the tank, in accordance with one embodiment of the invention.
Figure 16:
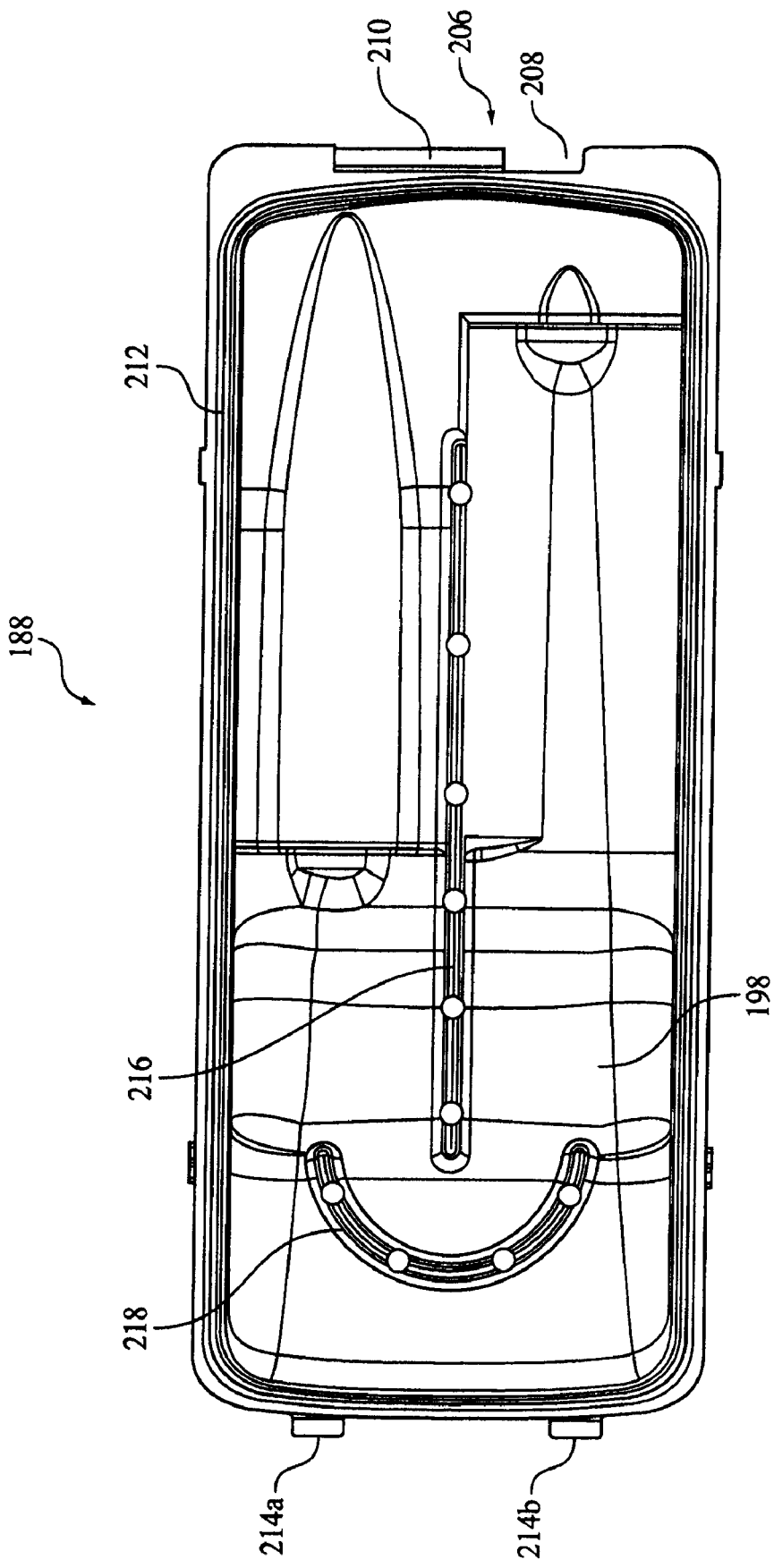
FIG. 16 is a bottom elevation of the upper tank housing, according to one embodiment of the invention.

Turning briefly to FIG. 15, a bottom perspective view of upper tank housing 188 is illustrated. In FIG. 15, a vaulted region formed by elevated portion 198 is illustrated, as are the pair of tabbed protrusions (illustrated as tabbed protrusions 214a and 214b). On the under side of upper tank housing 188, a dividing ridge 216 is formed as a substantially vertical protrusion that extends out of the cavity formed by upper tank housing 188. Dividing ridge 216 runs substantially down the middle of upper tank housing 188. At the front end of tank 16, an arched ridge 218 is formed that extends down out of the vaulted region created by elevated portion 198. The configuration of ridges 216 and 218 is illustrated further in FIG. 16, which is an elevational bottom view of upper tank housing 188. Dividing ridge 216 and arched ridge 218, among other things, directs and channels the flow of gas from the inlet to the outlet of the tank to ensure that the gas mixes with the vapor arising from the fluid contained in the tank.

Returning to FIG. 14, lower tank housing 190 is shown as including a plurality of tank housing struts 220 (illustrated as tank housing struts 220a-220f) that provide strength to lower tank housing 190, and provide guidance and support for other components during assembly. A lower tank housing rim 222 is formed around the edge of lower tank housing 190. Just within lower tank housing rim 222, a seal ledge 224 is formed. At the back end of tank 16, a catch 226 is provided on lower tank housing 190. Catch 226 includes a tabbed member 228, and is slideable in a substantially horizontal direction along the edge of lower tank housing 190. At the front end of tank 16, a pair of tab engaging members 230 (illustrated as tab engaging members 230a and 230b) form tab openings 232 (illustrated as tab openings 232a and 232b).

Also located at the front of tank 16, a tank window opening 234 is formed in the wall of lower tank housing 190. A window cover 236 is disposed over tank window opening 234, and protrudes outward from lower tank housing 190. In one embodiment, window cover 236 is composed of a clear material so that the interior of tank 16 may be viewed through tank window opening 234. At a bottom surface of lower tank housing 190 a conductor opening 238 is formed. Tank window opening 234 window cover 236 allow the user to view the contents of tank 14. This is important, for example, in monitoring the level of the fluid in the tank. Thus, window cover 236 is a clear, semi-clear, or opaque material that allows the user to view the level of fluid in the tank.

As is shown in FIG. 14, tank 16 also includes a heat conductor 240 that has a shape that corresponds substantially to conductor opening 238. Heat conductor 240 is composed of a material that is capable of conducting heat from outside tank 16 to the interior of the tank. For example, in one embodiment, heat conductor 240 is formed from stainless steel. Heat conductor 240 is assembled to lower tank housing 190 by positioning heat conductor 240 within conductor opening 238 and attaching heat conductor 240 to a retaining lip 242. Since an outer edge of each of heat conductor 240 and retaining lip 242 are somewhat larger than conductor opening 238, attaching heat conductor 240 to retaining lip 242 secures heat conductor 240 in position. A conductor seal 244 is disposed between heat conductor 240 and retaining lip 242 to seal the interface between heat conductor 240, retaining lip 242, and lower tank housing 190 at conductor opening 238. In one embodiment, heat conductor 240 and retaining lip 242 are attached via a pressure-fit. However, in other embodiments, alternative methods for attaching heat conductor 240 and 242 may be employed. In one embodiment, alternative sealing mechanisms may be employed in place of conductor seal 244. For example, a gasket or an overmolded seal may be implemented.

To couple upper tank housing 188 to lower tank housing 190, housings 188 and 190 are positioned such that tabbed protrusions 214a and 214b slide through tab openings 232a and 232b, and engage tab engaging members 230a and 230b. Then, housings 188 and 190 are pivoted with respect to each other until upper tank housing rim 212 is positioned within lower tank housing rim 222 and rests on a housing seal 209 that provides a seal between housings 188 and 190. In order to pivot housings 188 and 190 into this position, catch 226 is positioned so that tabbed portion 228 will fit into cut-out 208 of catch engaging region 206. Once housings 188 and 190 are pivoted into position, catch 226 is slid so that tabbed portion no long fits into cut-out 208, but instead engages ledge 210. The tank housings 188 and 190 may be uncoupled to enable a reservoir of fluid (e.g., water) held by tank 16 to be cleaned, and/or refilled.

Figure 17:
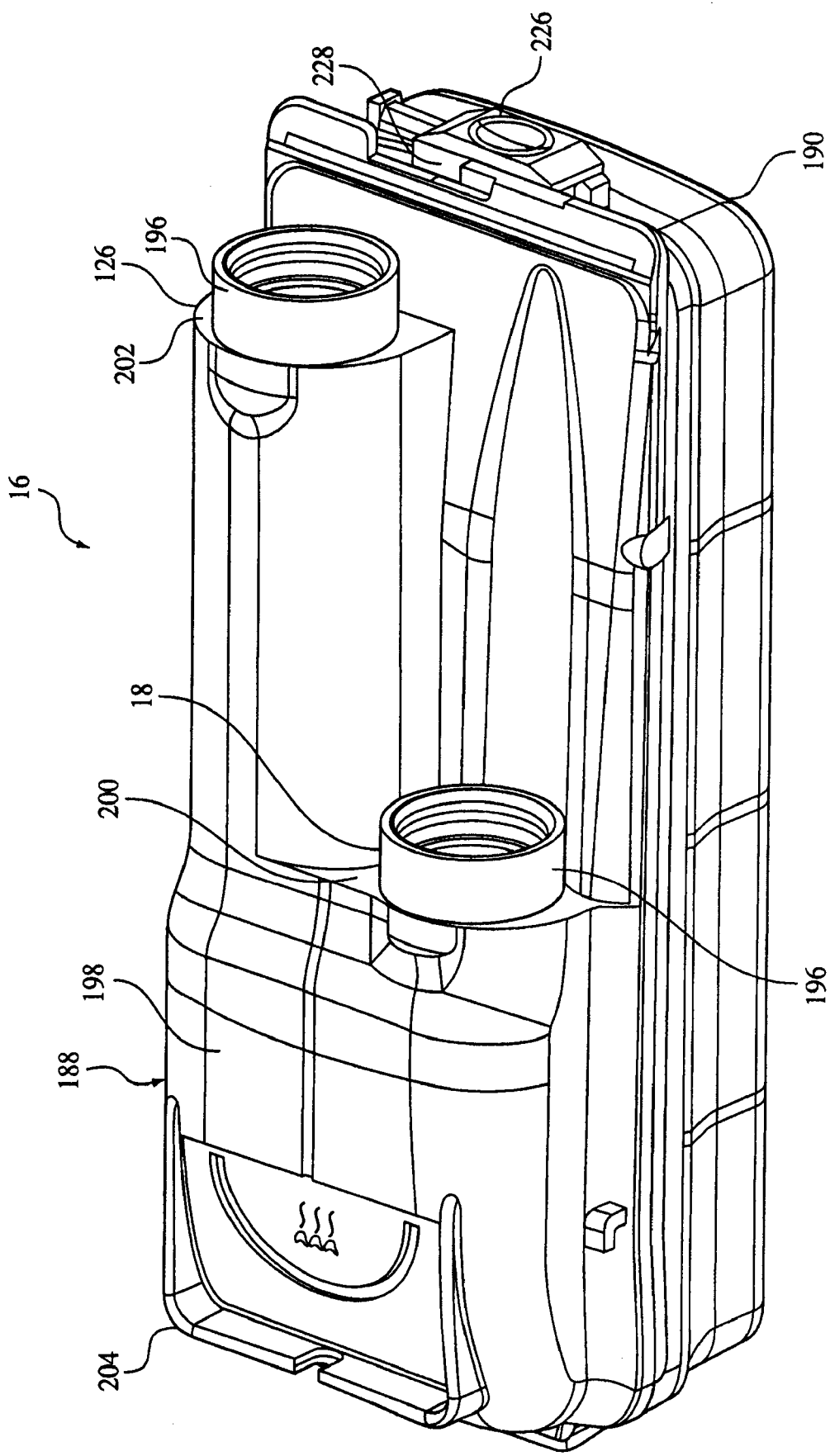
FIG. 17 illustrates the tank assembled according to one embodiment of the invention.

FIG. 17 shows tank 16 fully assembled with tank housings 188 and 190 coupled together. When tank 16 is assembled and implemented in pressure support system 10, various operating conditions may cause the reservoir of fluid held by tank 16 to be spilled from one or both of tank inlet 18 and tank outlet 20. One such phenomenon may include situations in which tank 16 is transported, or jostled, which may cause waves in the reservoir of fluid. Arched ridge 218 formed within upper tank housing 188 may reduce spillage associated with these, and other waves created within the reservoir of fluid, by causing the waves to destructively interfere with themselves. Another cause of spillage is tilting tank 16.

However, tank 16 includes various features designed to minimize spillage due to tilting. For example, if tank 16 is tilted towards its rear end, the vaulted region formed by elevated portion 198 is able to accommodate most, if not all of the reservoir of fluid, so that virtually none of the fluid will be spilled tank inlet 18. If tank 16 is tilted towards the side on which tank outlet 20 is located, or towards the front end, the extension of elevated portion 198 further toward the front end of tank 16 on the side of tank 16 on which tank outlet 20 is located will channel the fluid toward tank outlet 20 to ensure that most, if not all of the fluid spilled will be lost out of tank outlet 20, instead of tank inlet 18. This may protect various components of patient system 10 in communication with tank inlet 18, such as electronic components such as sensors and/or circuit boards. Other measures to counteract spillage from tank 16 are described below.

Figure 18:
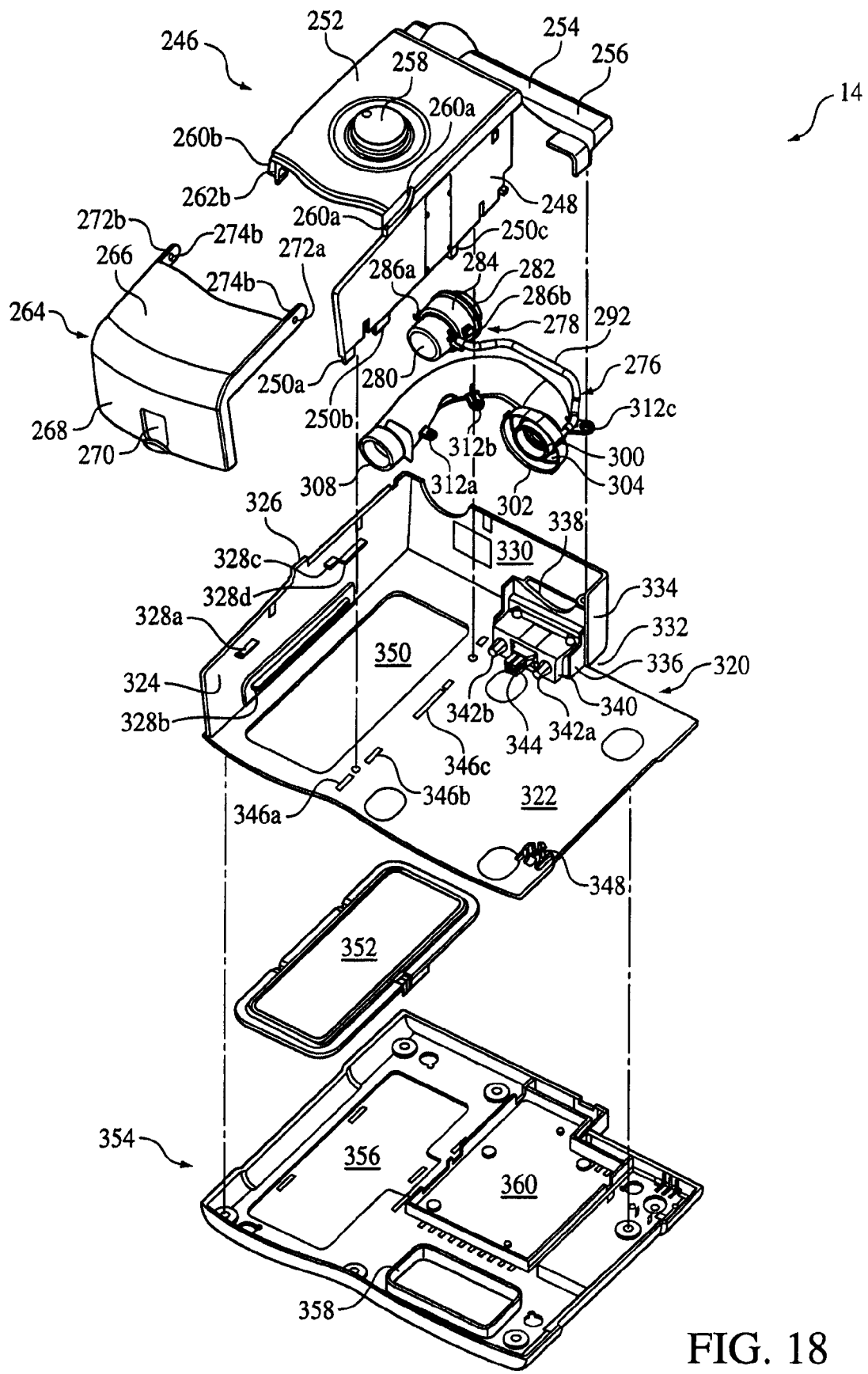
FIG. 18 is a partially exploded view of a docking assembly included in the pressure support system, in accordance with one embodiment of the invention.

FIG. 18 is an exploded view of docking assembly 14, according to one embodiment of the invention. Docking assembly 14 includes a tank cover assembly 246. A wall structure 248 is disposed at a side of tank cover assembly 246 that is oriented toward the interior of docking assembly 14, and forms a substantially vertical surface. One or more wall structure tabs 250 (illustrated as tabs 250a-250c) extend downward from a lower edge of wall structure 248. At an upper edge, wall structure 248 meets a top cover structure 252 that provides a substantially horizontal surface at the top of tank cover assembly 246. A cover assembly protrusion 254 extends rearward and laterally toward the interior of docking assembly 14 from a rear edge of top cover structure 252, and provides a substantially horizontal ledge 256.

Disposed on top cover structure 252 is a humidifier control interface 258. In one embodiment, humidifier control interface 258 includes a knob. However, in other embodiments, humidifier control interface may include any mechanism for enabling an individual to manipulate or control one or more various functions of docking assembly 14, as will be described hereafter. On each side of top cover structure 252, toward a front end of docking assembly 14, a door interface 260 (illustrated as door interfaces 260a and 260b) is provided. Each door interface 260 includes a slot 262 (illustrated as slots 262a and 262b).

As is shown in FIG. 18, docking assembly 14 includes a tank door 264. Tank door 264 is formed substantially as an upper door structure 266 and a front door structure 268. A door opening 270 is formed in front door structure 268. Extending from upper door structure 266 are two cover interfaces 272a and 272b. Each of cover interfaces 272a and 272b include a protrusion 274 (illustrated as protrusions 274a and 274b).

Figure 19:
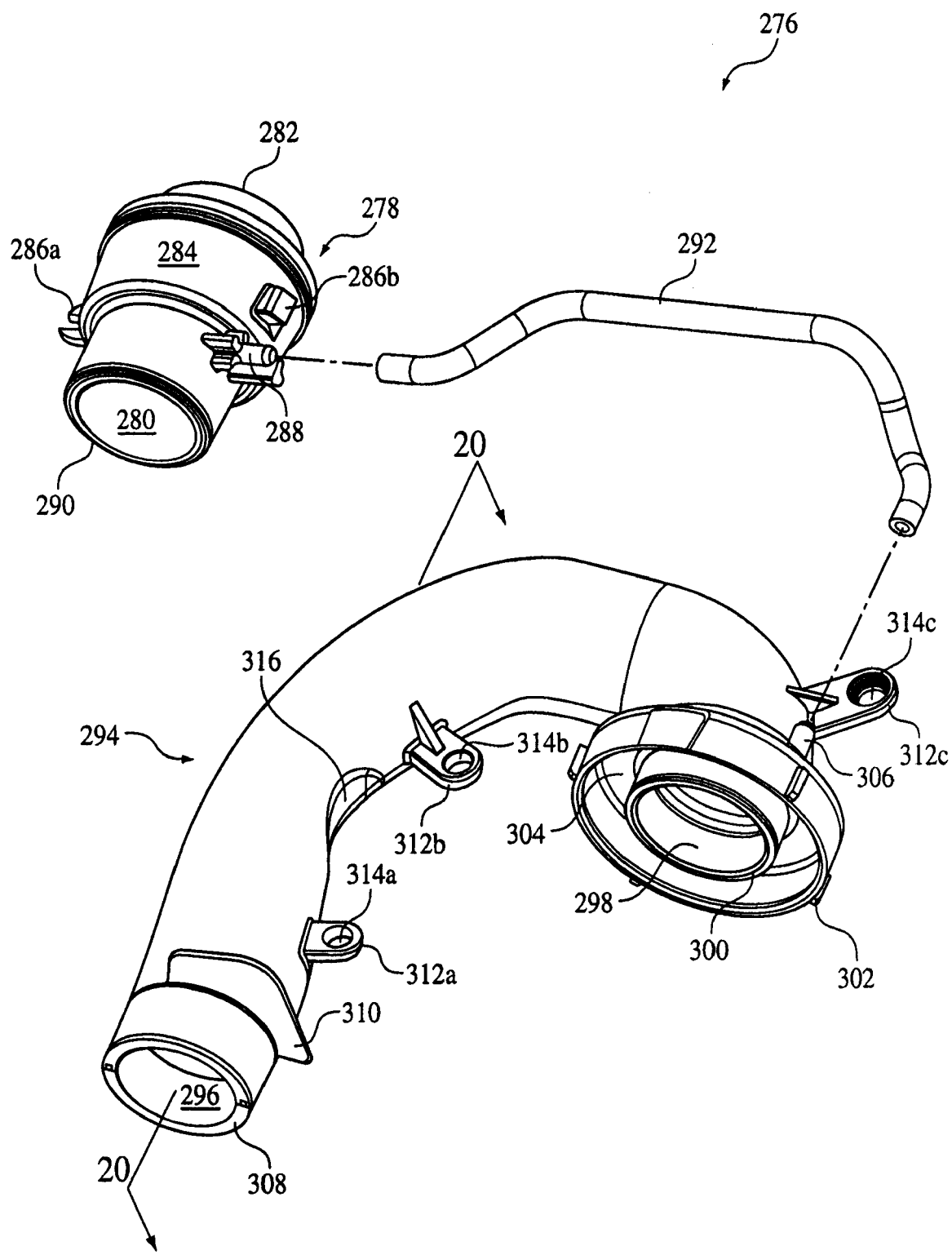
FIG. 19 is an exploded view of a conduit docking assembly included in the docking assembly, according to one embodiment of the invention.

A docking conduit assembly 276 included in docking assembly 14 is illustrated in FIG. 18, and a larger, exploded view of docking conduit assembly 276 is shown in FIG. 19. Docking conduit assembly 276 includes an outlet conduit 278. Outlet conduit 278 forms a pathway 280, through which the pressurized flow of breathable gas may flow. At an end of outlet conduit 278 that extends out of docking assembly 14, an annular ridge 282 is formed that enables patient conduit 22 to interface with outlet conduit 278. A middle portion 284 of outlet conduit 278 is formed with an expanded outer diameter relative to the rest of outlet conduit 278. Outlet conduit protrusions 286 (illustrated as protrusions 286a and 286b) extend from middle portion 284 of outlet conduit 278. A bypass vent 288, formed as a hollow protrusion that communicates with pathway 280, extends from outlet conduit 278. At an end of outlet conduit 278 that extends into docking assembly 14, a tank outlet interface 290 is formed.

As is shown in FIG. 19, docking conduit assembly 276 includes a bypass conduit 292. In one embodiment, bypass conduit 292 may be formed from a flexible material, such as a polymer, or another flexible material.

Docking conduit assembly 276 includes an inlet conduit 294 that forms a pathway 296 through which the pressurized flow of breathable gas may pass. At one end of inlet conduit 294, a docking assembly inlet 298 is formed. Docking assembly inlet 298 includes an inner annular ridge 300 and an outer annular ridge 302 formed coaxially with inner annular ridge 300. Inner annular ridge 300 and outer annular ridge 302 define an annular groove 304.

Figure 20:
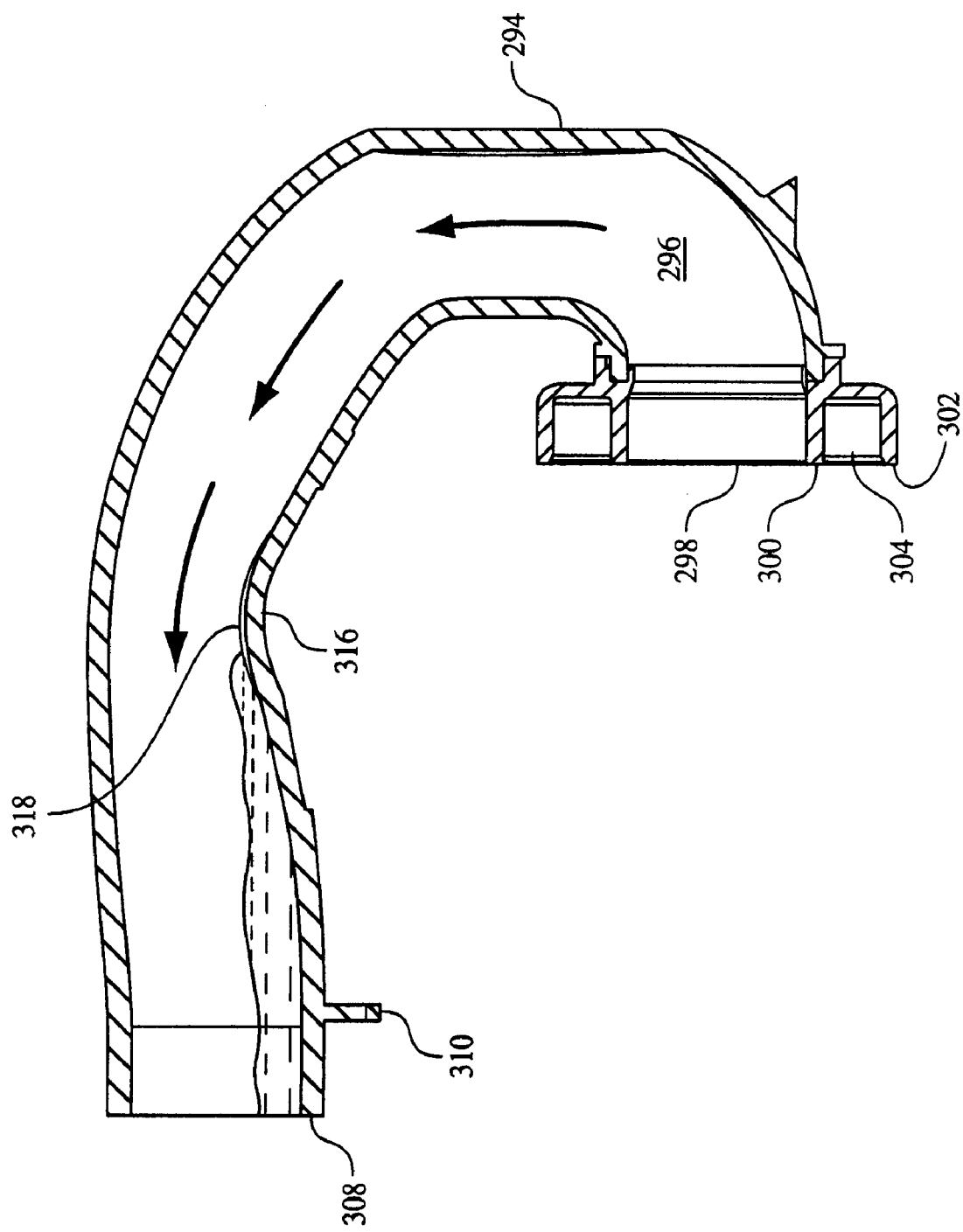
FIG. 20 is a sectional view of an inlet conduit, taken along section lines 20-20 shown in FIG. 19, included in conduit docking assembly, according to one embodiment of the invention.

A bypass vent 306, formed as a hollow protrusion from docking assembly inlet 300 communicates with annular groove 304. At an end of inlet conduit 294 opposite docking assembly inlet 298, a tank inlet interface 308 is formed. Proximate to tank inlet interface 308, a planar conduit protrusion 310 extends outward from inlet conduit 294. A plurality of support structures 312 (illustrated as support structures 312a-312c) extend from several locations along inlet conduit 294. Each of support structures 312 includes a fastener opening 314 (illustrated fastener openings 314a-314c). In one embodiment, when viewed from above, inlet conduit 294 generally forms a "J" shape, with tank inlet interface 308 disposed at the top of the long side of the J, and docking assembly inlet 298 formed at the top of the short side of the J. Along the long side of the J formed by inlet conduit 294, an indention 316 is formed. FIG. 20 shows a sectional view of inlet conduit 294 that illustrates how indention 316 forms a barrier 318 within inlet conduit 294.

Returning to FIG. 18, docking conduit assembly 276 is assembled by inserting bypass vents 288 and 306 into opposite ends of bypass conduit 292. When docking conduit assembly 276 is assembled, bypass conduit enables pathway 280 formed by outlet conduit 278 to communicate with annular groove 304.

Figure 22:
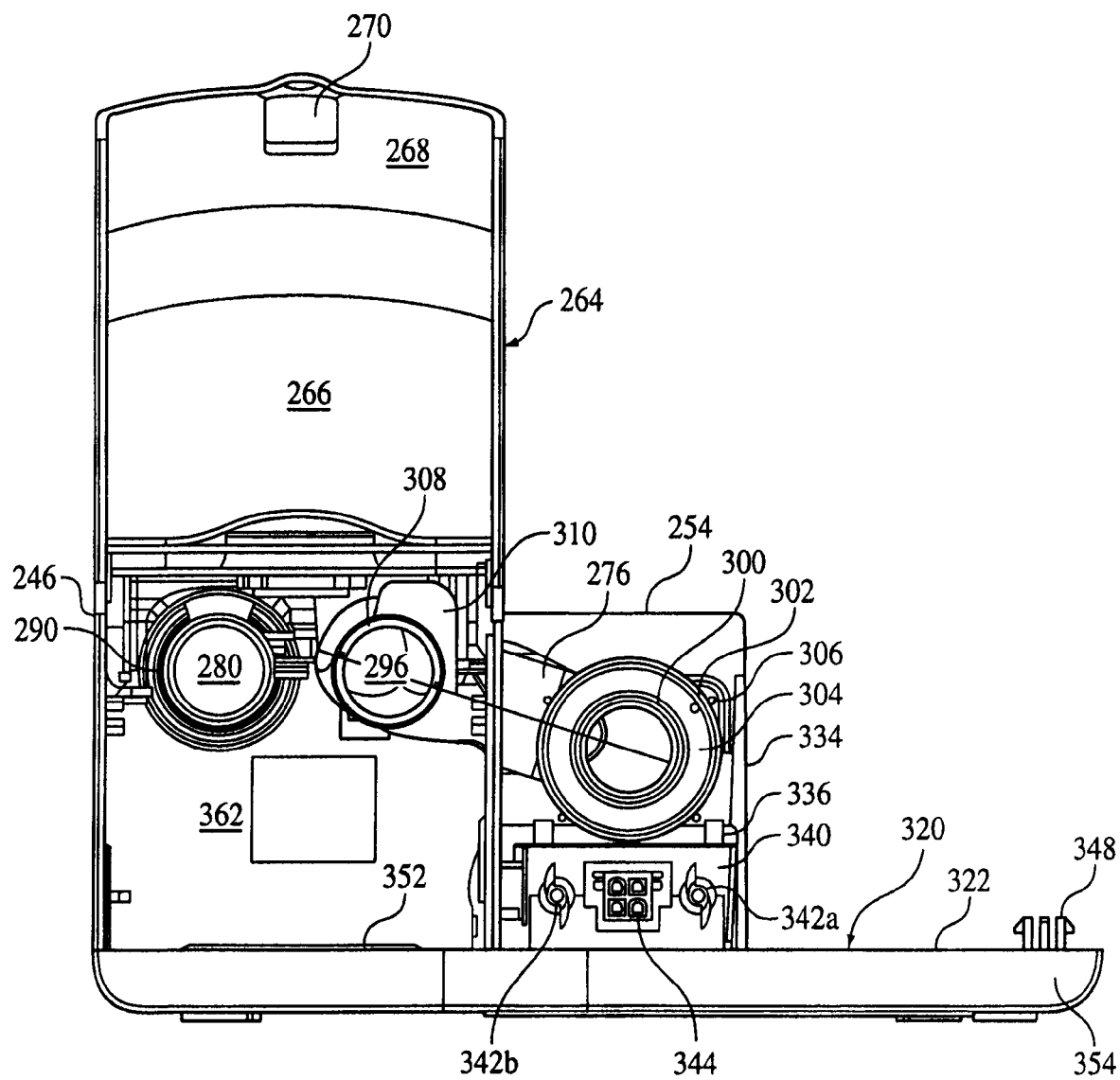
FIG. 22 is a front elevation of the docking assembly, in accordance with one embodiment of the invention.

As can be seen in FIG. 18, docking assembly 14 includes an upper base assembly 320. Upper base assembly 320 includes a base floor 322 formed as a substantially horizontal, planar structure. Along an edge of base floor 322, a side wall structure 324 extends away from base floor 322 in a substantially vertical plane. A side wall tab 326 extends vertically upwards from side wall structure 324. Guide protrusions 328 (illustrated as guide protrusions 328a-328d) extend inward from side wall structure 324 in a substantially horizontal direction. Although not labeled, the present invention contemplates (and FIG. 22 illustrates) similar guide protrusions provided on opposing wall 248. The guide protrusions cooperate with tank 16 to facilitate insertion of the tank into a tank cavity 362 such that tank inlet 18 and outlet 20 properly align with tank outlet interface 290 and tank inlet interface 308 and so that heat conductor 240 is properly seating on a heating element 352.

A rear wall structure 330 extends away from base floor 322 in a substantially vertical direction along a rear edge of base floor 322. Rear wall structure 330 is formed to the side of base floor 322 at which side wall structure 324 is formed, such that wall structures 324 and 330 join to form a corner. A jog 332 is formed in the rear edge of base floor 322, and a jog wall structure 334 extends vertically upward from the edge of base floor 322 at jog 332, forming a corner with rear wall structure 330.

Upper base assembly 320 includes a connector housing 336. Connector housing 336 is disposed at the corner formed by rear wall structure 330 and jog wall structure 334. A conduit support member 338 is provided on an upper surface of connector housing 336. Connector housing 336 includes a housing face 340. On housing face 340, a pair of stops 342 (illustrated as stops 342a and 342b). Between stops 342, a connector 344 is provided. Upper base assembly 320 includes a plurality of slots 346 (illustrated as slots 346a-346c) formed therein. A delivery system engaging protrusion 348 protrudes out of the upper surface of upper base assembly 320.

A heating element opening 350 is formed in upper base assembly 320 proximate to wall structures 324 and 330. FIG. 18 shows a heating element 352 included in docking assembly 14. Heating element 352 is provided with a shape that corresponds substantially to heating element opening 350 formed in upper base assembly 320. Heating element 352 is a body that is controllably heated. In one embodiment, heating element 352 is composed of a metallic material, and is configured so that when an electrical current is supplied to heating element 352, the temperature of heating element 352 increases and heat is radiated therefrom. For example, heating element 352 may include an aluminum shell enclosing a steel body that is heated by the electrical current.

Docking assembly 14 includes a lower base assembly 354. Lower base assembly 354 forms a shallow cavity with a shape that substantially corresponds to the outer footprint of upper base assembly 320. Lower base assembly 354 includes a heating element seating portion 356 with a shape corresponding to the shape of heating element 352. In one embodiment, heating element seating portion 356 includes a heat resistive (or insulating) layer disposed within the cavity formed by lower base assembly 354. A support ridge 358 is formed extending up vertically from lower base assembly 354. Lower base assembly 354 includes an electronics seating portion 360 formed and adapted to seat electronics such as one or more circuit boards (not shown) or other electrical components.

Figure 21:
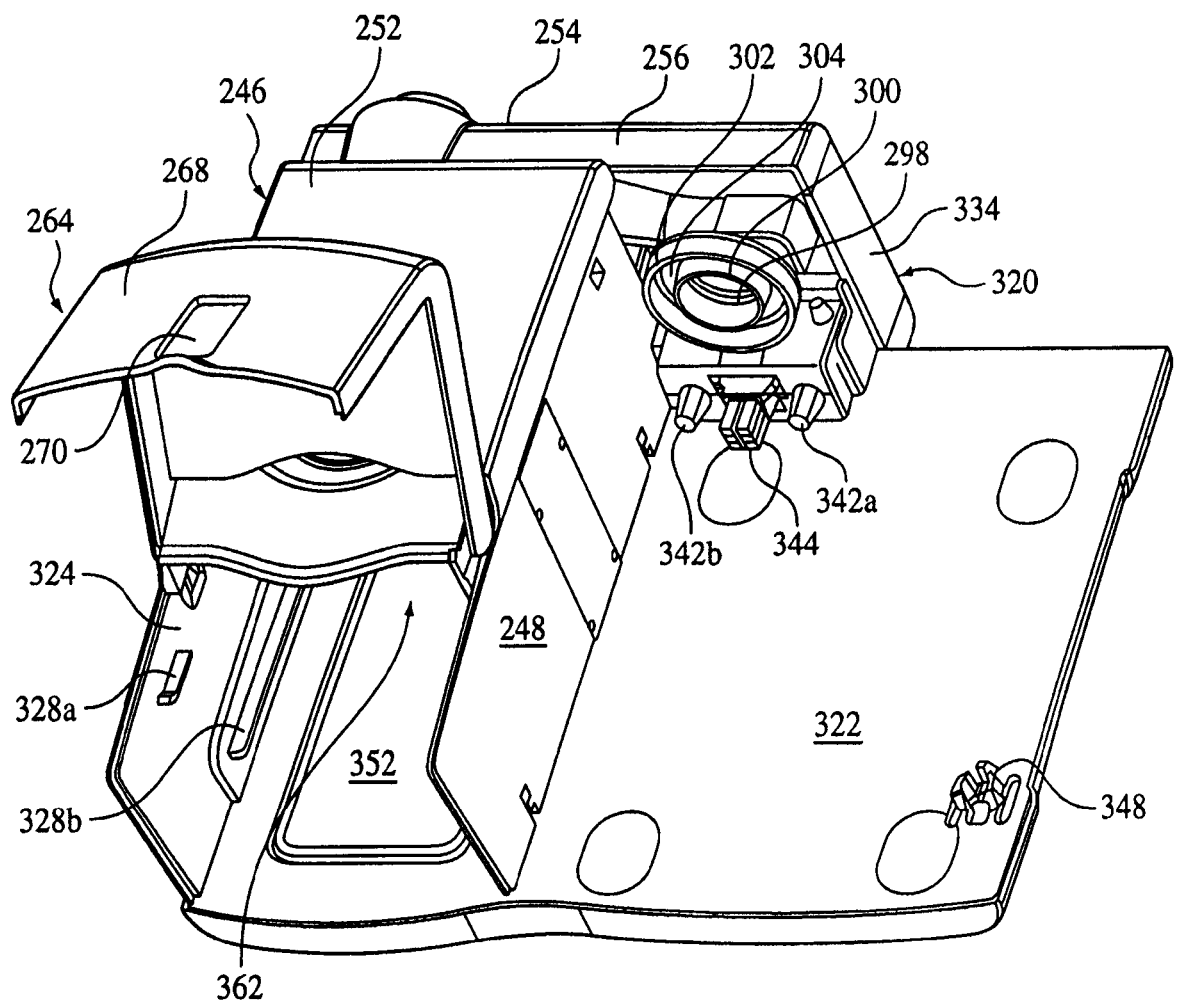
FIG. 21 illustrates the docking assembly assembled according to one embodiment of the invention.

FIG. 21 illustrates docking assembly 14 fully assembled, in accordance with an embodiment of the invention. Tank cover assembly 246 is joined to upper base assembly 320 such that wall structure 248, cover structure 252, wall structure 324, base floor 322, and heating element 352 form a tank cavity 362. When tank cover assembly 246 is joined to upper base assembly 320, tabs 250 fit into slots 346 (best seen in FIG. 18), and protrusion 326 extending from wall structure 324 fits into a corresponding slot (not shown) formed in tank cover assembly 246. Additionally, cover assembly protrusion 254 lines up with, and contacts lower base assembly 320 along a top edge of wall structures 330 and 334.

Cover interfaces 272 extending from tank door 264 are pivotably joined to door interfaces 260 formed on tank cover assembly 246 by inserting protrusions 274 into slots 262. As can be seen in the elevation view of the front of assembled docking assembly 14 shown in FIG. 22, docking conduit assembly 276 is disposed at the rear end of docking assembly 14 between tank cover assembly 246 and upper base assembly 320. In particular, conduit support member 338 supports inlet conduit 294, protrusion 304 abuts tank cover assembly 246, and outlet conduit 278 is supported by an opening formed by protrusion 256 and wall structure 330. Further, although not visible in the view shown in FIG. 22, support structures 312 act to support docking conduit assembly 276 in the position illustrated. As can be seen in FIG. 22, tank inlet interface 308 and tank outlet interface 290 formed by docking conduit assembly 276 are disposed within tank cavity 362.

Upper base assembly 322 and lower base assembly 354 are joined at the rim of the cavity formed by lower base assembly 354. Heating element 352 is secured between base assemblies 322 and 354 such that heating element 352 sits on heating element seating portion 356, and is exposed to tank cavity 362 via heating element opening 350. The various components of docking assembly 14 may be joined to one another via a variety of methods, such as, for example, ultrasonic welding, an adhesive substance, fasteners, a press-fit, a friction-fit, a snap-fit, another method, or some combination thereof.

In one embodiment of the invention, some or all of the electronic components included within docking assembly 14 are connected to each other for communication and/or power. For example, heating element 352, the electronics seated within docking assembly 14 at electronics seating portion 360, humidifier control interface 258, and electrical connection 344 may be connected to each other. Additionally, in one embodiment of the invention, a power connection that is accessible for connecting an external power source is disposed on an outer surface of wall structure 330, and the power connection is also linked to the other electronic components listed above. In this embodiment, the electronics seated at electronics seating portion 360 may include a control unit that controls an electrical current that is supplied to heating element 352 to control an amount of heat radiated from heating element 352. The electrical current may be controlled by the control unit based on input from an individual, such as a patient or caregiver, received via humidifier control interface 258.

Gas flow generating system 12 can be used alone or in combination with docking assembly 14. When used with docking assembly 14, gas flow generating is removably placed in communication with docking assembly 14 by positioning gas flow generating system 12 such that docking interface 68 is positioned such that annular lip 94 of gas flow generating system 12 contacts docking assembly inlet 298 so that each of inner annular ridge 300 and outer annular ridge 302 form a substantially sealed connection with annular lip 94. The substantially sealed passage created by the connection between inner annular ridge 300 and annular lip 94 enables the pressurized flow of breathable gas that is output from gas flow generating system 12 at outlet opening 92 to be introduced to docking assembly 14 via inlet conduit 294. The substantially sealed connection between outer annular ridge 302 and annular lip substantially seals annular groove 304 from ambient atmosphere and the pressurized flow of breathable gas being communicated between outlet opening 92 and inlet conduit 294. Since opening 98 of pressure conduit 96 is formed in annular lip 94 such that opening 98 communicates with annular groove 304 when docking assembly inlet 298 contacts annular lip 94, a substantially sealed connection is created between bypass conduit 292 and pressure conduit 96.

As gas flow generating system 12 is placed in communication with docking assembly 14, stops 342 formed on housing face 340 of connector housing 336 contact docking port recesses 100 to position gas flow generating system 12 properly on docking assembly 14. Connectors 102 and 344 interface, creating an operative link between gas flow generating system 12 and docking assembly 14. In one embodiment, the operative link between gas flow generating system 12 and docking assembly 14 includes an electrical connection, and a control signal is communicated between gas flow generating system 12 and docking assembly 14 via the electrical connection. Protrusion 348 interfaces with a slot (not shown) formed on the bottom side of gas flow generating system 12, and secures gas flow generating system 12 in place on docking assembly 14.

As can be seen in FIG. 1B, assembling pressure support system 10 includes removably placing tank 16 in tank cavity 362. As tank 16 is brought to the position within tank cavity 362 illustrated in FIG. 1A, tank seal 196 disposed at tank inlet 18 connects with tank inlet interface 298 to form a substantially sealed passage therebetween, through which the pressurized flow of breathable gas is delivered from gas flow generating system 12 to tank 16 by way of inlet conduit 294. As tank 16 is removably placed within tank cavity 362, tank seal 196 disposed at tank outlet 20 connects with tank outlet interface 290 of outlet conduit 278 to form a substantially sealed passage between outlet conduit 278 and tank 16 such that the pressurized flow of breathable gas received into tank 16 at tank inlet 18 can be received into outlet conduit 278.

When positioned within tank cavity 362, heat conductor 240 of tank 16 rests on, or over, heating element 352, and conducts heat radiated from heating element 352 to the interior of tank 16. Guide protrusions 328 formed within tank cavity 362 act to guide tank 16 into tank cavity 362, and tank door 264 is closed to enclose tank 16 in tank cavity and to secure tank 16 therein. Door opening 270 formed in tank door 264 corresponds to tank window opening 234, and openings 270 and 234 enables an individual to view a level of the reservoir of fluid contained in tank 16 without opening tank door 264 and/or removing tank 16 from tank cavity 362. When tank 16 is positioned within tank cavity 362 as shown in FIG. 1A, tank 16 is removed by engaging handle ridge 204 and pulling tank 16 out of tank cavity 362.

When tank 16 and gas flow generating system 12 are placed in communication with docking assembly 14, as illustrated in FIG. 1A, and the pressurized flow of breathable gas is being directed through tank 16, heating element 352 may be controlled to radiate heat such that a configurable amount of heat is supplied to the reservoir of water held by tank 16. Providing heat to the reservoir of water will produce water vapor in tank 16 which, in turn, will elevate a humidity level of the pressurized flow of breathable gas as it passes through tank 16. By controlling an amount of heat radiated by heating element 352, an amount by which the humidity level of the pressurized flow of breathable gas is elevated may be controlled.

In one embodiment of the invention, a portion of the gas included the pressurized flow of breathable gas being delivered to the patient from tank 16 via outlet conduit 278 communicated from outlet conduit 278 to the pressure sensor included within gas flow generating system 12 via bypass vent 288, bypass conduit 292, bypass vent 306, annular groove 304, and pressure conduit 96. In this embodiment, a bypass circuit is formed, including bypass vent 288, bypass conduit 292, and bypass vent 306, that returns a portion of the gas included in the pressurized flow of breathable gas to gas flow generating system 12 from a location downstream from tank 16, which enables the pressure of the pressurized flow of breathable gas to be controlled as it is output from docking assembly 14.

As was mentioned previously, when pressure support system 10 is assembled, it can be problematic if fluid from the reservoir of fluid held by tank 16 is spilled into inlet conduit 294, and passed through inlet conduit 294 to gas flow generating system 12. One set of circumstances not discussed above which may result in such spillage, is when pressure support system 10 is tilted such that tank 16 is positioned above gas flow generating system 12. In instances where this occurs some of the fluid may flow out of tank inlet 18 and into inlet conduit 294. However, as is illustrated in FIG. 20, this flow of fluid may be impeded by barrier 316 formed within 316. Additionally, barrier 316 may act on the pressurized flow of breathable gas such that the flow pattern of the gas is shaped to blow the fluid away from flowing over barrier 316 and into gas flow generating system 12.

Figure 23:
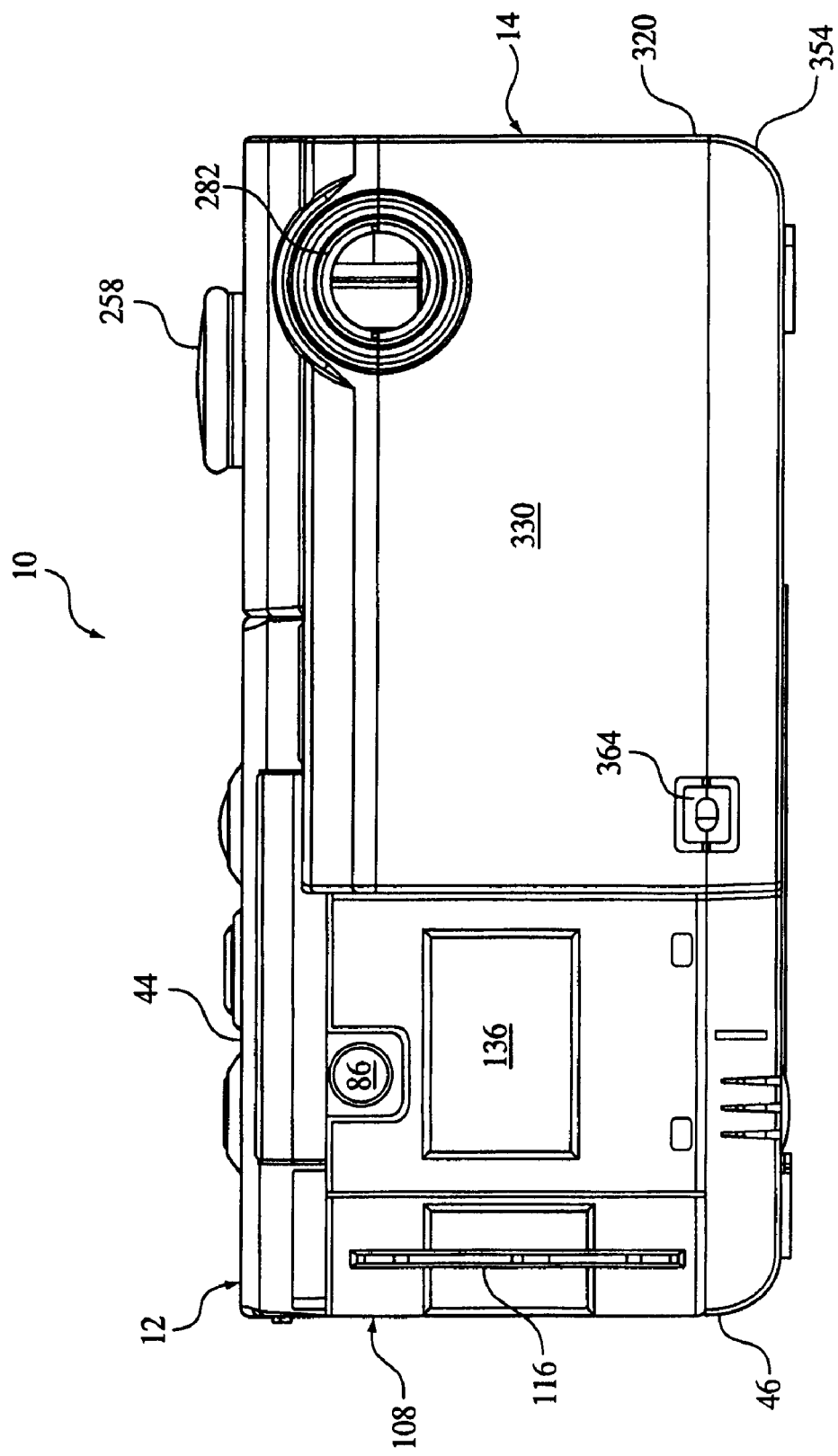
FIG. 23 is a rear elevation of the pressure support system, according to one embodiment of the invention.

FIG. 23 illustrates a rear elevation of pressure support system 10, according to an embodiment of the invention. FIG. 23 shows a docking assembly power connection 364 through which docking assembly 14 receives power from an external power source. FIG. 23 also shows delivery system power connection 86. In one embodiment of the invention, docking assembly 14 is adapted to run on AC power and gas flow generating system 12 is adapted to run on DC power. In another embodiment, power connection 364 may be eliminated and docking assembly 14 is adapted to on DC power that is supplied to docking assembly 14 via the connection between gas flow generating system 12 and docking assembly 14. Of course, gas flow generating system 12 or docking assembly 14 can be powered by internal power supplies, such as batteries, contained in each component or shared therebetween.

Figure 24:
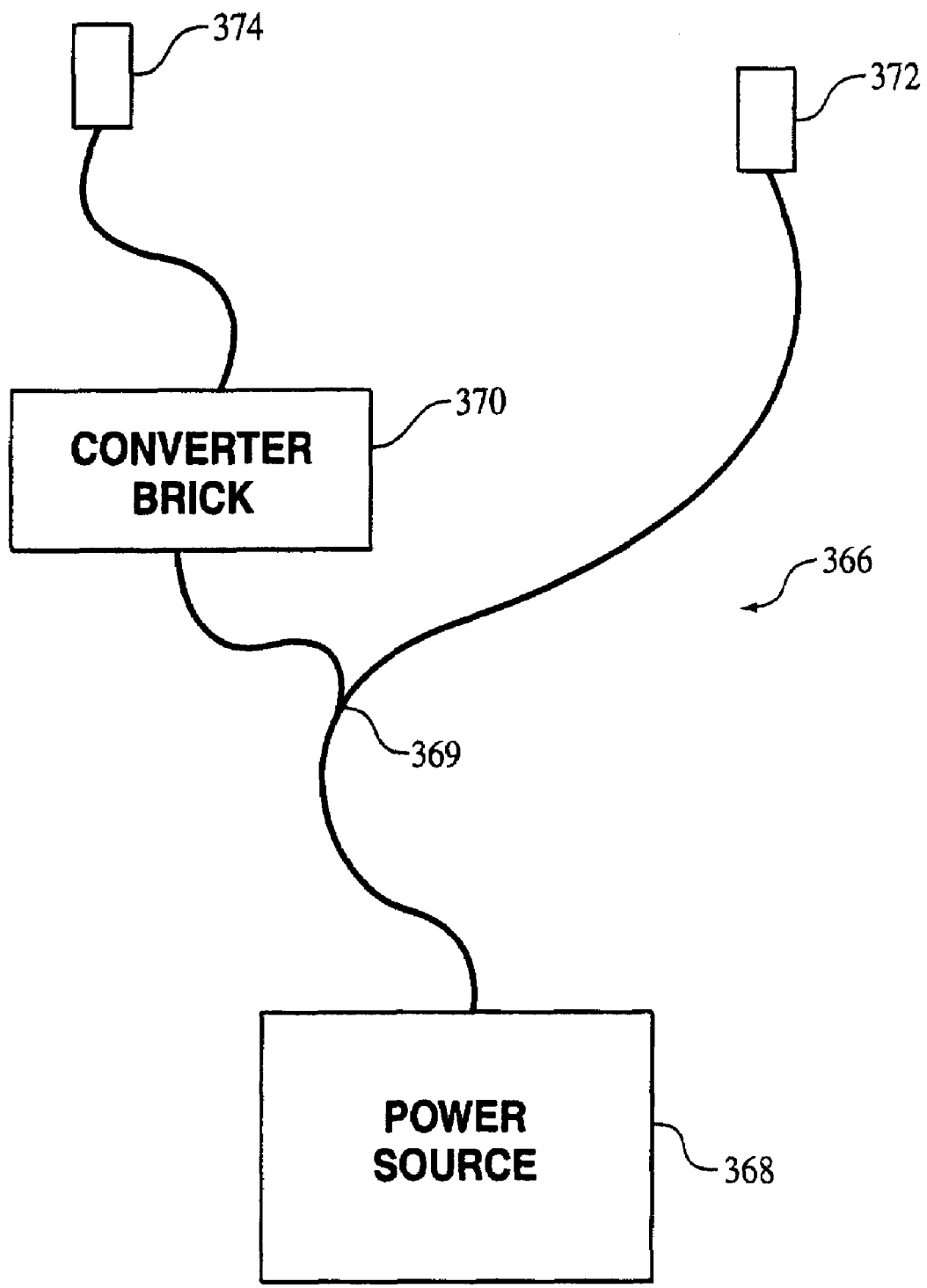
FIG. 24 is a schematic representation of a power cable capable of providing power to the pressure support system from an external power source, in accordance with one embodiment of the invention.

FIG. 24 illustrates a power cable 366 that is configured to provide power to both docking assembly 14 and gas flow generating system 12 from a single AC power source 368. In one embodiment, power source 368 is a wall outlet. Power cable 366 includes a junction 369 a converter brick 370 an AC power connector 372 and a DC power connector 374. Power is transmitted from power source 368 to junction 369 At junction 369, the power from power source 368 is divided. AC power is carried directly from junction 369 to AC power connector 372. AC power is also carried from junction 369 to converter brick 370 where the AC power is converted to DC power that is then provided to DC power connector 374. By connecting AC power connector 372 to docking assembly power connection 364 and connecting DC power connector 374 to gas flow generating system power connection 86, both docking assembly 14 and gas flow generating system 12 are simultaneously powered by power source 368. In one embodiment, AC power connector 372 is hardwired to docking assembly 14 at docking assembly power connection 364. In another embodiment, this connection is detachable.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support system comprising:
   a gas flow generating system adapted to generate a flow of breathable gas;
   a patient circuit adapted to deliver a pressurized flow of breathable gas to a patient;
   a tank adapted to contain a supply of liquid; and
   a docking assembly having an inlet adapted to be coupled to the gas flow generating system to receive the flow of breathable gas, and an outlet adapted to be connected to the patient circuit, wherein the docking assembly includes a tank housing portion defining a chamber adapted to receive at least a portion of the tank responsive to the tank being coupled to the docking assembly.

2. The pressure support system of claim 1, therein the tank is constructed and arranged to be removably connected with the tank housing portion of the docking assembly such that the tank is disposed between the inlet and the outlet.

3. The pressure support system of claim 1, wherein the gas flow generating system is removably connected with the inlet of the docking assembly.

4. The pressure support system of claim 3, wherein the docking assembly comprises a first docking circuit and a second docking circuit, and the tank comprises a tank inlet and a tank outlet, and wherein the patient circuit and the tank outlet are each removably connected with the first docking circuit such that the pressurized flow of breathable gas is enabled to flow between the tank outlet and the patient circuit via the first docking circuit, and the tank inlet and the gas flow generating system are each removably connected with the second docking circuit such that the pressurized flow of breathable gas is enabled to flow between the tank inlet and the gas flow generating system via the second docking circuit.

5. The pressure support system of claim 1, further comprising:

a pressure sensor that measures a flow rate of the pressurized flow of breathable gas; and a pressure bypass circuit that interfaces with the docking assembly to receive a portion of the pressurized flow of breathable gas flowing between the tank and the patient circuit, and delivers the portion of the pressurized flow of breathable gas to the pressure sensor, wherein the pressure bypass circuit is formed separate from the tank.

6. The pressure support system of claim 1, wherein the docking assembly comprises a heating element that heats the liquid held by the tank.

7. The pressure support system of claim 6, wherein the heating element heats the liquid by heating an external surface of the tank.

8. The pressure support system of claim 3, wherein the docking assembly comprises a first connector and the gas flow generating system comprises a second connector that is detachably connected to the first connector to form a connection between the docking assembly and the gas flow generating system.

9. The pressure support system of claim 8, wherein the docking assembly comprises a heating element that heats the liquid held by the tank, and a sensor associated with the heating element, and wherein information related to the heat of the liquid held by the tank is transmitted between the docking assembly and the gas flow generating system via the connection between first connector of the docking assembly and the second connector of the gas flow generating system.

10. The pressure support system of claim 9, further comprising a control interface provided on the docking assembly, the control interface enables an individual to control one or more aspects of operation of the pressure support system.

11. A gas flow generating system that generates a pressurized flow of breathable gas for delivery to a patient, the system comprising:

a control unit that controls one or more aspects of operation of the gas flow generating system; and an accessory interface that removably connects with a modular accessory to place the modular accessory in communication with the control unit such that information can be transferred from the modular accessory to the control unit and from the control unit to the modular accessory via the accessory interface.

12. The gas flow generating system of claim 11, wherein the information transferred from the modular accessory to the control unit comprises information related to at least one of a calibration of the gas flow generating system or a configuration of the gas flow generating system.

13. The gas flow generating system of claim 11, wherein the information transferred from the control unit to the modular accessory comprises (a) information related to the pressurized flow of breathable gas, (b) an amount of breathable gas delivered to the patient, (c) an amount of time during which the pressurized flow of breathable gas has been delivered to the patient, or (d) a combination thereof.

14. The gas flow generating system of claim 11, further comprising a housing that substantially encloses the gas flow generating system, wherein connecting the modular accessory with the accessory interface positions the modular accessory substantially within the housing.

15. A pressure support system comprising:

a patient circuit adapted to deliver a pressurized flow of breathable gas to a patient;

a docking assembly having an inlet and an outlet, the inlet adapted to receive the pressurized flow of breathable gas, the outlet adapted to be connected with the patient circuit, wherein the docking assembly includes a tank housing portion;

a pressure sensor adapted to measure a flow rate of the pressurized flow of breathable gas; and a pressure bypass circuit adapted to interface with the docking assembly to receive a portion of the pressurized flow of breathable gas flowing between the tank and the patient circuit, and deliver the portion of the pressurized flow of breathable gas to the pressure sensor, wherein the pressure bypass circuit is formed separate from the tank.

16. A pressure support system comprising:

a patient circuit adapted to deliver a pressurized flow of breathable gas to a patient;

a gas flow generating system adapted to generate a pressurized flow of breathable gas; and a docking assembly having an inlet and an outlet, the inlet adapted to receive the pressurized flow of breathable gas from the gas flow generating system, the outlet adapted to be connected with the patient circuit, wherein the docking assembly includes:

a tank housing portion, a first connector, adapted to detachably couple to an outlet of the gas flow generating system to form a connection between the docking assembly and the gas flow generating system, a heating element adapted to that heat liquid held by a tank responsive to the tank be provided in the tank housing portion, and a sensor associated with the heating element, and wherein information related to heating of the liquid held by the tank is transmitted between the docking assembly and the gas flow generating system via the first connector.

* * * * *